United States Patent
Wells et al.

(10) Patent No.: US 10,874,552 B2
(45) Date of Patent: Dec. 29, 2020

(54) OCULAR LENS CUTTING DEVICE

(75) Inventors: Trent Spencer Wells, Los Angeles, CA (US); Matthew T. McCormick, Los Angeles, CA (US); Ralph Kerns, Los Angeles, CA (US); Mark S. Humayun, Los Angeles, CA (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 1868 days.

(21) Appl. No.: 14/130,888

(22) PCT Filed: Jul. 5, 2012

(86) PCT No.: PCT/US2012/045607
§ 371 (c)(1),
(2), (4) Date: Aug. 28, 2014

(87) PCT Pub. No.: WO2013/009576
PCT Pub. Date: Jan. 17, 2013

(65) Prior Publication Data
US 2014/0364885 A1    Dec. 11, 2014

Related U.S. Application Data

(60) Provisional application No. 61/505,959, filed on Jul. 8, 2011.

(51) Int. Cl.
*A61F 9/007*    (2006.01)
*A61B 17/30*    (2006.01)

(52) U.S. Cl.
CPC ...... *A61F 9/00763* (2013.01); *A61F 9/00754* (2013.01); *A61B 2017/306* (2013.01)

(58) Field of Classification Search
CPC ........ A61B 17/3207; A61B 17/320016; A61B 2017/306; A61B 10/0233–0291;
(Continued)

(56) References Cited

U.S. PATENT DOCUMENTS 3,732,858 A    5/1973 Banko
3,882,872 A    5/1975 Douvas et al.
(Continued)

FOREIGN PATENT DOCUMENTS

| EP | 0 310 285 A2 | 4/1989 |
|---|---|---|
| JP | 2002-177317 | 6/2002 |
| JP | 2006-015984 | 1/2006 |
| JP | 2010512963 | 4/2010 |
| WO | WO93005718 | 4/1993 |
| WO | WO 98/52502 | 11/1998 |
| WO | WO2008029066 | 3/2008 |
| WO | WO 2010/118172 A1 | 10/2010 |

OTHER PUBLICATIONS

Japanese Office Action, Application No. 2014520223; with English translation; 9 pages, dated Nov. 13, 2015.
(Continued)

*Primary Examiner* — Tan-Uyen T Ho
*Assistant Examiner* — Charles M Wei
(74) *Attorney, Agent, or Firm* — Snell & Wilmer LLP

(57) ABSTRACT

Ocular lens cutting devices and methods for cutting and removing tissue such as lens fragments from an eye of a patient are disclosed. In one embodiment, an ocular lens cutting device includes an outer member and an inner member positioned within the outer member. The outer member and the inner member can each include at least one cutting edge. The at least one cutting edge of the outer member and the at least one cutting edge of the inner member can cooperate to form a cutting structure as the inner member moves with respect to the outer member. The ocular lens cutting device can also be connected to a vacuum source which can allow the ocular lens cutting device to grasp the tissue to be cut and remove the cut fragments from the surgical area.

14 Claims, 18 Drawing Sheets

(58) Field of Classification Search
CPC .......... A61B 17/32053; A61B 17/3205; A61B 17/3209; A61B 17/16; A61B 17/32; A61B 17/32002; A61B 17/320708; A61B 17/32075; A61B 17/320758; A61B 17/320783; A61B 2017/320024; A61B 2017/320028; A61B 2017/320741; A61B 2017/320775; A61B 2017/320064; A61B 2017/320072; A61B 2017/320076; A61B 2017/32008; A61F 9/00736; A61F 9/00754; A61F 9/00763
USPC ................ 606/107, 114, 115, 167, 171, 178
See application file for complete search history.

(56) References Cited

U.S. PATENT DOCUMENTS

| | | | |
|---|---|---|---|
| 3,937,222 A | 2/1976 | Banko | |
| 3,976,077 A | 8/1976 | Kerfoot, Jr. | |
| 3,990,453 A | 11/1976 | Douvas et al. | |
| 4,011,869 A * | 3/1977 | Seiler, Jr. ............ | A61F 9/00763 604/22 |
| 4,111,207 A * | 9/1978 | Seiler, Jr. ............ | A61F 9/00763 30/241 |
| 4,167,944 A | 9/1979 | Banko | |
| 4,368,734 A * | 1/1983 | Banko ................. | A61F 9/00763 606/107 |
| 4,428,748 A | 1/1984 | Peyman et al. | |
| 4,449,550 A * | 5/1984 | Ranalli ............... | A61F 9/00763 137/624.13 |
| 4,508,532 A | 4/1985 | Drews et al. | |
| 4,530,356 A | 7/1985 | Helfgott et al. | |
| 4,590,935 A * | 5/1986 | Ranalli ............... | A61F 9/00763 604/22 |
| 4,598,710 A | 7/1986 | Kleinberg et al. | |
| 4,662,869 A | 5/1987 | Wright | |
| 4,757,814 A | 7/1988 | Wang et al. | |
| 4,811,734 A * | 3/1989 | McGurk-Burleson ...................... A61F 9/00763 30/240 | |
| 4,844,064 A * | 7/1989 | Thimsen .......... | A61B 17/32002 30/240 |
| 4,850,354 A | 7/1989 | McGurk-Burleson et al. | |
| 4,867,157 A * | 9/1989 | McGurk-Burleson ...................... A61B 17/32002 30/240 | |
| 4,895,166 A | 1/1990 | Farr et al. | |
| 4,908,015 A | 3/1990 | Anis | |
| 4,909,249 A | 3/1990 | Akkas et al. | |
| 4,911,161 A | 3/1990 | Schechter | |
| 4,940,468 A | 7/1990 | Petillo | |
| 4,983,179 A | 1/1991 | Sjostrom | |
| 4,986,827 A | 1/1991 | Akkas et al. | |
| 5,047,008 A | 9/1991 | De Juan, Jr. et al. | |
| 5,084,052 A * | 1/1992 | Jacobs ............. | A61B 17/32002 606/170 |
| 5,106,364 A * | 4/1992 | Hayafuji .......... | A61B 17/32002 30/208 |
| 5,112,339 A | 5/1992 | Zelman | |
| 5,139,504 A | 8/1992 | Zeiman | |
| 5,346,497 A | 9/1994 | Simon et al. | |
| 5,391,180 A | 2/1995 | Tovey et al. | |
| 5,403,276 A | 4/1995 | Schechter et al. | |
| 5,423,844 A | 6/1995 | Miller | |
| 5,437,630 A * | 8/1995 | Daniel ............. | A61B 17/32002 604/22 |
| 5,464,389 A | 11/1995 | Stahl | |
| 5,492,528 A | 2/1996 | Anis | |
| 5,562,691 A | 10/1996 | Tano et al. | |
| 5,613,972 A | 3/1997 | Lee et al. | |
| 5,630,827 A * | 5/1997 | Vijfvinkel ......... | A61B 10/0266 604/22 |
| 5,690,660 A | 11/1997 | Kauker et al. | |
| 5,722,945 A | 3/1998 | Anis et al. | |
| 5,730,718 A | 3/1998 | Anis et al. | |
| 5,746,713 A | 5/1998 | Hood et al. | |
| 5,766,194 A * | 6/1998 | Smith ............... | A61B 17/3203 606/1 |
| 5,782,849 A * | 7/1998 | Miller .............. | A61B 17/32002 604/22 |
| 5,792,167 A | 8/1998 | Kablik et al. | |
| 5,807,401 A | 9/1998 | Grieshaber et al. | |
| 5,827,292 A | 10/1998 | Anis | |
| 5,843,111 A * | 12/1998 | Vijfvinkel ........ | A61B 10/0266 604/22 |
| 5,911,699 A * | 6/1999 | Anis ................ | A61F 9/00745 604/22 |
| 6,007,513 A | 12/1999 | Anis et al. | |
| 6,007,556 A | 12/1999 | Kablik et al. | |
| 6,024,751 A * | 2/2000 | Lovato ............. | A61B 1/015 604/22 |
| 6,027,514 A | 2/2000 | Stine et al. | |
| 6,203,518 B1 | 3/2001 | Anis et al. | |
| 6,217,543 B1 | 4/2001 | Anis et al. | |
| 6,258,111 B1 | 7/2001 | Ross et al. | |
| 6,342,061 B1 | 1/2002 | Kauker et al. | |
| 6,352,519 B1 | 3/2002 | Anis et al. | |
| 6,478,681 B1 * | 11/2002 | Overaker .......... | A61B 17/1624 464/29 |
| 6,488,695 B1 | 12/2002 | Hickingbotham | |
| 6,514,268 B2 | 2/2003 | Finlay et al. | |
| 6,540,695 B1 | 4/2003 | Burbank et al. | |
| 6,629,986 B1 | 10/2003 | Ross et al. | |
| 6,638,235 B2 | 10/2003 | Miller et al. | |
| 6,730,106 B2 | 5/2004 | Kanda et al. | |
| 6,773,445 B2 | 8/2004 | Finlay et al. | |
| 7,013,566 B1 | 3/2006 | Bellm et al. | |
| 7,083,608 B2 | 8/2006 | Tomita et al. | |
| 7,276,032 B2 | 10/2007 | Hibner | |
| 7,470,277 B2 | 12/2008 | Finlay et al. | |
| 7,758,537 B1 | 7/2010 | Brunell et al. | |
| 8,092,378 B2 * | 1/2012 | Roth ................ | A61B 17/0218 600/206 |
| 8,092,472 B2 * | 1/2012 | Cerier .............. | A61B 1/313 606/139 |
| 8,172,865 B2 | 5/2012 | DeBoer et al. | |
| 8,858,461 B2 * | 10/2014 | Persat ............. | A61B 10/0275 600/562 |
| 2001/0031976 A1 * | 10/2001 | Lobdell ............ | A61F 9/00763 606/171 |
| 2002/0052617 A1 | 5/2002 | Anis et al. | |
| 2003/0060841 A1 | 3/2003 | Del Rio et al. | |
| 2003/0144606 A1 | 7/2003 | Kadziauskas et al. | |
| 2003/0236471 A1 * | 12/2003 | Fisher ............. | A61B 10/0266 600/573 |
| 2004/0049217 A1 | 3/2004 | Ross et al. ....... | 606/171 |
| 2004/0158236 A1 | 8/2004 | Thyzel | |
| 2005/0165436 A1 * | 7/2005 | Ichikawa ......... | A61F 9/00763 606/171 |
| 2005/0256512 A1 | 11/2005 | Del Rio et al. | |
| 2006/0036270 A1 | 2/2006 | Terao | |
| 2006/0281599 A1 | 12/2006 | Murakami et al. | |
| 2007/0088376 A1 | 4/2007 | Zacharias | |
| 2007/0129732 A1 | 6/2007 | Zacharias | |
| 2007/0185512 A1 | 8/2007 | Kirchhevel | |
| 2007/0185514 A1 | 8/2007 | Kirchhevel | |
| 2007/0191758 A1 | 8/2007 | Hunter et al. | |
| 2008/0021487 A1 * | 1/2008 | Heisler ............ | A61B 17/32002 606/170 |
| 2008/0045986 A1 * | 2/2008 | To .................. | A61B 17/320708 606/159 |
| 2008/0146965 A1 | 6/2008 | Privitera et al. | |
| 2008/0149197 A1 | 6/2008 | Turner et al. | |
| 2008/0172078 A1 | 7/2008 | Svetic | |
| 2008/0188881 A1 | 8/2008 | Chon | |
| 2008/0208233 A1 | 8/2008 | Barnes et al. | |
| 2009/0069831 A1 * | 3/2009 | Miller ............. | A61B 17/32 606/171 |
| 2009/0082715 A1 | 3/2009 | Charles | |
| 2009/0287233 A1 | 11/2009 | Huculak | |
| 2012/0022434 A1 * | 1/2012 | Lue ................ | A61F 9/00763 604/22 |

(56) References Cited

U.S. PATENT DOCUMENTS

| | | | |
|---|---|---|---|
| 2012/0101513 A1* | 4/2012 | Shadeck | A61B 17/1659 606/170 |
| 2012/0221033 A1* | 8/2012 | Auld | A61F 9/00763 606/170 |
| 2015/0133771 A1* | 5/2015 | Marczyk | A61B 5/065 600/424 |
| 2015/0133985 A1* | 5/2015 | Vetter | A61B 10/0266 606/171 |
| 2016/0022489 A1* | 1/2016 | Hartstra | A61F 9/00763 606/166 |

OTHER PUBLICATIONS

Written Opinion Received in PCT/US07/088745 dated Jul. 2, 2009.
U.S. Appl. No. 14/256,726, including its prosecution history, the references cited therein and the Office Actions therein, Apr. 18, 2014, Barnes, et al.
Extended European Search Report dated May 24, 2011 in European Application No. 07865997.6.
International Preliminary Report on Patentability and Written Opinion dated Oct. 20, 2011 in PCT/US2010/030296 filed on Apr. 7, 2010.
International Search Report and Written Opinion Received in PCT/US08/078087 dated Apr. 6, 2009.
International Search Report and Written Opinion Received in PCT/US2010/030296 dated May 21, 2010.
International Search Report dated Jun. 2, 2008 in PCT/US2007/088745.
Office Action dated Aug. 3, 2012 for Japanese Patent Application No. 2009-543284.
International Preliminary Report on Patentability in PCT/US2007/088745 dated Jun. 24, 2009.
International Preliminary Report on Patentability dated Mar. 30, 2010 in PCT/US2008/078087.
Supplemental European Search Report dated May 10, 2011 for European Application No. 07865997.6 filed Dec. 21, 2007.

* cited by examiner

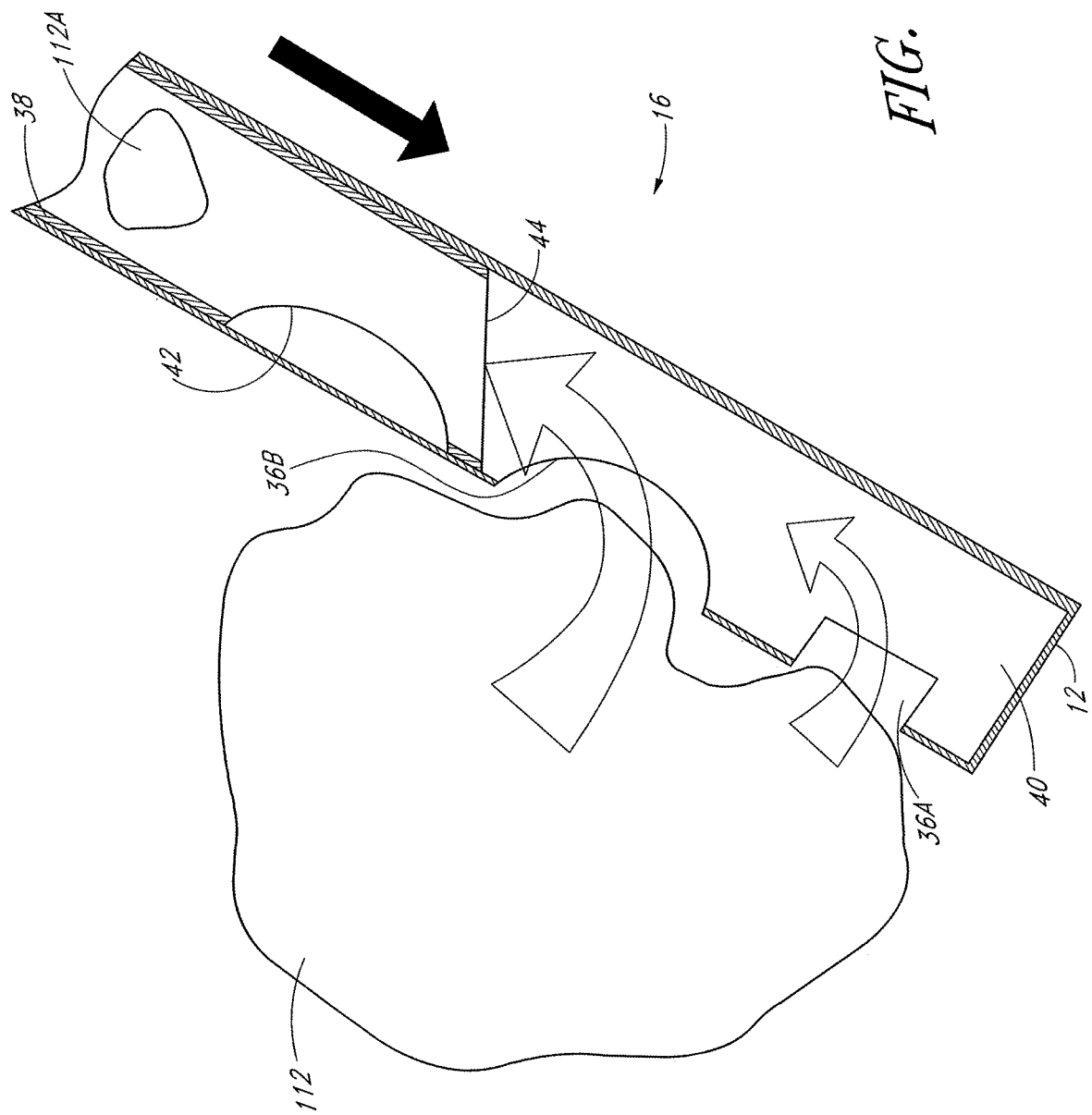

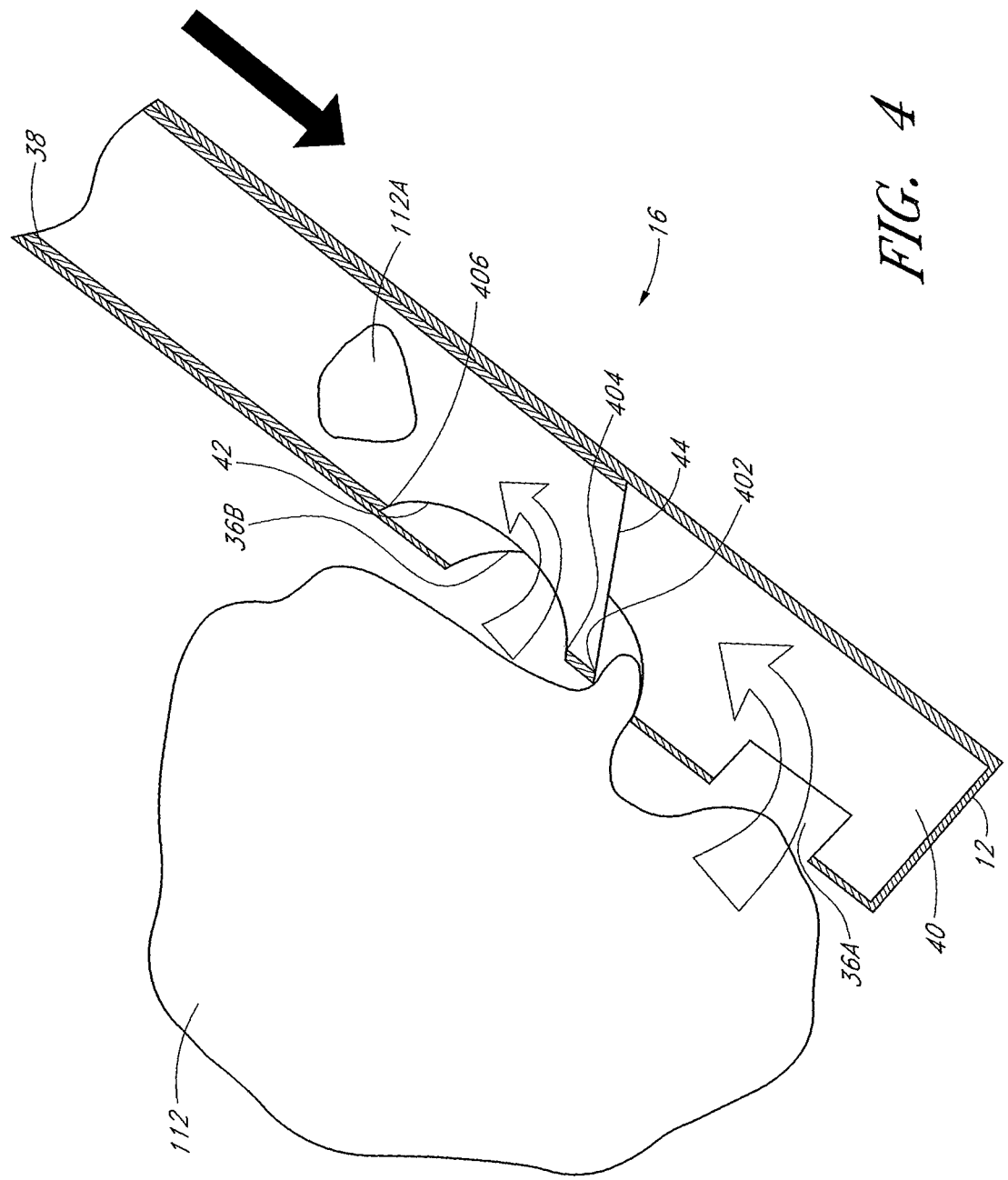

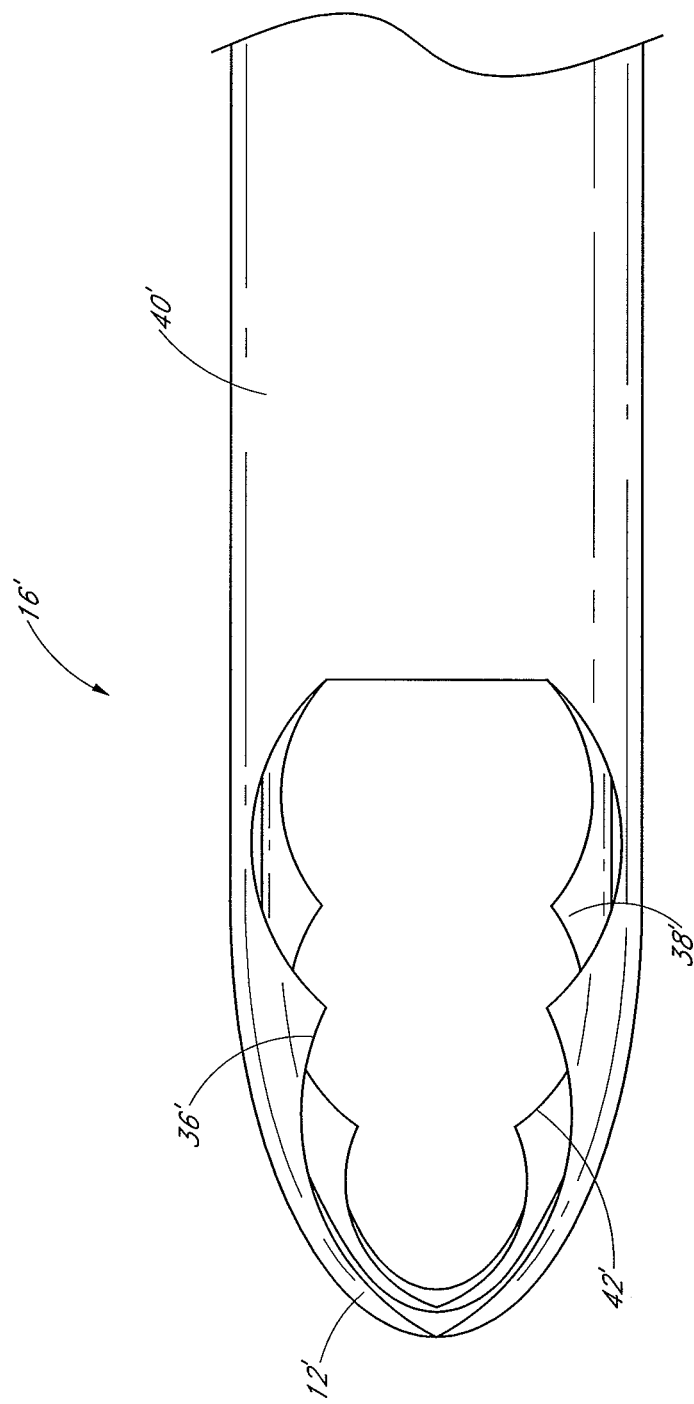

OCULAR LENS CUTTING DEVICE

CROSS-REFERENCE TO RELATED APPLICATIONS

This application is a PCT Application, which claims the benefit of U.S. Provisional Application No. 61/505,959, filed Jul. 8, 2011 and titled OCULAR LENS CUTTING DEVICE. This application is related to PCT International Application No. PCT/US2010/030296, filed Apr. 7, 2010, published as WO 2010/118172, the entire content of which is incorporated by reference herein.

FIELD

Certain embodiments herein relate generally to tissue cutter technology, and more particularly to systems, methods, and devices for facilitating the cutting and removal of tissue, such as with an ocular lens cutting device. Various embodiments described herein further relate to phacomorcellation devices, systems, and methods for cutting and removing eye tissue (e.g., lens fragments) during ophthalmic surgery.

BACKGROUND

Ophthalmic surgery often involves removal of eye tissue. For example, cataract surgery generally requires the removal and replacement of the lens. An artificial lens or intraocular lens implant can then be implanted within the eye to restore or improve the eyesight of the patient. Other procedures may also involve the removal of lens tissue and/or other types of eye tissue.

There are a number of procedures and devices that have been developed for the removal of eye tissue. For example, phacoemulsification is a widely used method for removal of diseased or damaged lens tissue. The phacoemulsification process generally involves insertion of a probe through a small corneal incision to break apart and remove the lens in cataract surgery.

In phacoemulsification, one or more incisions are generally made in the eye to allow the introduction of surgical instruments. The surgeon then removes the anterior face of the capsule that contains the lens inside the eye. An ultrasonic hand piece, where the tip vibrates at ultrasonic frequency, is generally used to sculpt and emulsify the cataract. After removal of the cataract, the posterior capsule is generally still intact and an intraocular lens implant (IOL) can be placed into the remaining lens capsule. At times during a phacoemulsification procedure, the capsule can rupture allowing lens fragments to fall into the eye and/or back onto the retina. This and other problems may occur during the procedure.

SUMMARY

There is a general need for improvement in ophthalmic surgery, including phacoemulsification processes and phacomorcellation or ocular lens cutting devices, systems and methods. There also exists a need for devices that can retrieve and/or remove lens fragments from the posterior portion of the eye and/or capture lens fragments up off the retina and remove the lens fragments. In some embodiments an ocular lens cutting device can be used to cut and/or remove eye tissue (for example, lens fragments), such as during ophthalmic surgery. In various embodiments, the ocular lens cutting device can remove lens fragments from the eye. In some embodiments the ocular lens cutting device can pick the lens fragment up off the retina and remove the lens fragment.

An ocular cutting device can have an outer housing for various internal components and a working end. The working end can be used to perform actions, such as during a surgical operation and can comprise various features including a cutting tip, aspiration features, and irrigation features.

In some embodiments, an ocular cutting device can have a housing, an aspiration line, and a working end. The working end can include an outer sleeve member coupled at the proximal end in fixed relationship to the housing and at a distal end having first and second openings. The first opening may include a first cutting edge. The working end can also include an inner sleeve member positioned within the outer sleeve member. A motor in the housing can be operatively coupled to the proximal end of the inner sleeve member to move the inner sleeve member relative to the outer sleeve member. The inner sleeve member can have a third opening with a second cutting edge and the first opening and third opening can be configured to interact to cut tissue between the first and second cutting edges.

Further, in some embodiments, the second opening of the outer sleeve can be configured to remain unobstructed by the movement of the inner sleeve such that vacuum applied to the working end through the aspiration line allows the second opening to grip a tissue mass at a first location of the tissue mass while the tissue is cut and removed by the working end at a second location of the tissue mass spaced from the first location.

Further, in some embodiments, the device can be configured such that part of the inner sleeve is positioned within the first opening during part of the time while tissue from the tissue mass is cut thereby increasing suction at the second opening.

The device can include a fourth opening on the inner sleeve having a third cutting edge, the fourth opening configured to interact with the first opening to cut tissue between the first and third cutting edges. The fourth opening can be an open distal end of the inner sleeve. In some embodiments, the third opening has a center axis perpendicular to the axis of the inner sleeve. In some embodiments, the first opening can have three generally circular or elliptical cutouts and the third opening can have two generally circular or elliptical cutouts.

According to some embodiments, an ocular cutting device can comprise a housing, a stationary outer tubular cutting member, a motor, an inner cutting member, and an aspiration line. The stationary outer tubular cutting member can have a proximal end and a distal end, the proximal end coupled to the housing, the distal end having a first port and a second port, the first port having a first cutting edge. The motor can be positioned within the housing and selectively controllable by one or more user control inputs coupled to the housing. The inner cutting member can have a proximal end and a distal end, the inner cutting member positioned within the stationary outer tubular cutting member, the motor coupled to the proximal end to move the inner cutting member relative to the stationary outer tubular cutting member, the inner cutting member having a second cutting edge at the distal end. The second port of the outer tubular cutting member can be configured to remain unobstructed by the movement of the inner cutting member to cut tissue such that vacuum applied to the working end through the aspiration line allows the second port to remain attached to tissue while tissue is cut and removed at the first port.

A method of using an ocular cutting device during surgery of the eye can comprise one or more of the following steps. Advancing a distal end of an ocular cutting device into a surgical site within the eye. The ocular cutting device can have an outer tubular cutting member having first and second openings at the distal end, the first opening having a first cutting edge; an inner cutting member having a third opening with a second cutting edge; and an aspiration line configured to apply a vacuum to the distal end of the ocular cutting device at the first and second openings. Applying said vacuum. Grasping a lens of an eye with the suction from the vacuum at the first and/or second openings of the ocular cutting device. Drawing a first portion of the lens into the first opening in the outer tubular cutting member. Fragmenting the first portion of the lens by moving the inner cutting member with respect to the outer tubular cutting member and cutting off the first portion of the lens at the first opening to create a first lens fragment, while at the second opening, the lens remains grasped by the ocular cutting device. Removing the first lens fragment from the surgical site through suction and through the outer tubular cutting member and/or inner cutting member.

A method according to some embodiments may also include the following additional steps. Wherein moving the inner cutting member comprises moving in at least one of a linear manner and a rotational manner with respect to the outer tubular cutting member. Drawing a second portion of the lens into the first opening in the outer tubular cutting member, and fragmenting the second portion of the lens by moving the inner cutting member with respect to the outer tubular cutting member and cutting off the second portion of the lens at the first opening to create a second lens fragment while at the second opening, the lens remains grasped by the ocular cutting device. Wherein the inner cutting member can further comprise a tubular member such that removing the lens fragment from the surgical site through suction and through the outer tubular cutting member further comprises removing the lens fragment through the inner cutting member. Wherein moving the inner cutting member with respect to the outer tubular cutting member may further comprise moving the first and second cutting edges to cut the first portion of the lens. Wherein the inner cutting member can further comprise a fourth opening and a third cutting edge, and moving the inner cutting member with respect to the outer tubular cutting member further comprises moving the first and third cutting edges to cut the first portion of the lens. Wherein grasping the lens of the eye further comprises removing the lens from off a retina of the eye.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIGS. 3-6B illustrate a distal end of an ocular lens cutting device and various methods of using the device.

FIG. 7 shows a distal end of an ocular lens cutting device.

DETAILED DESCRIPTION

Figure 1:
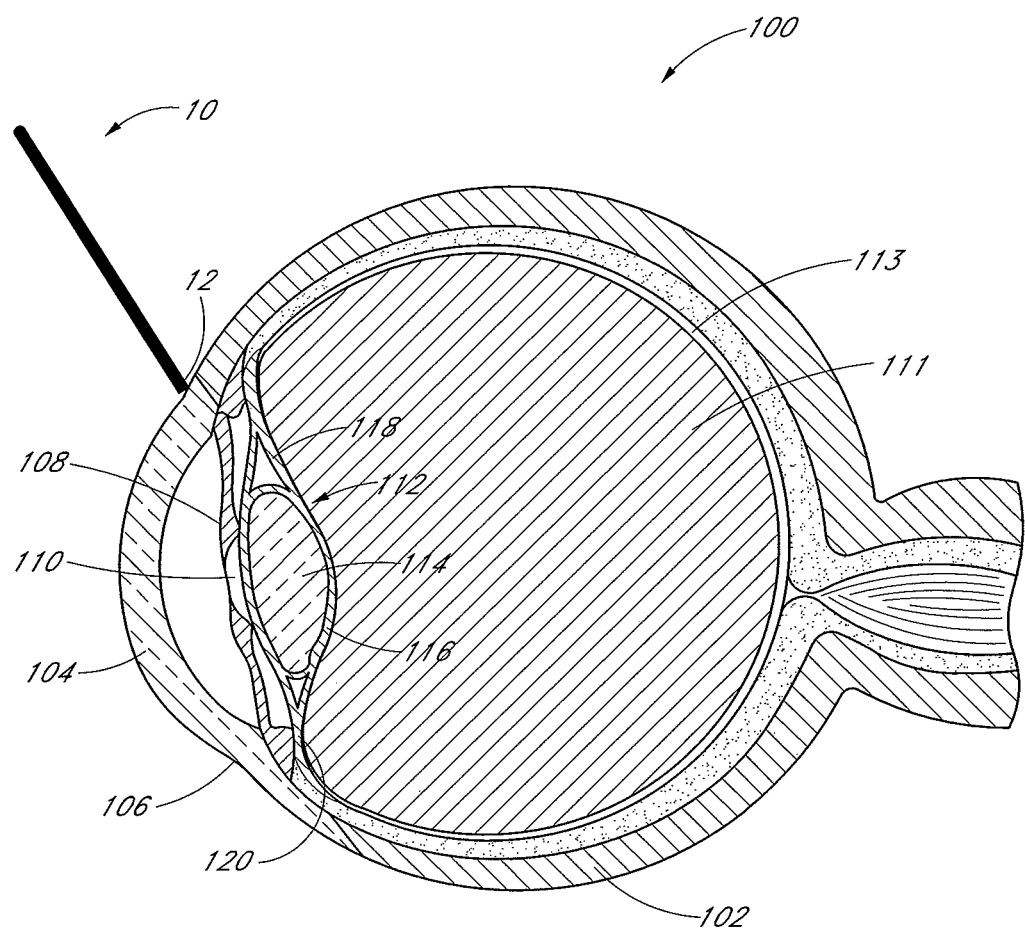
FIGS. 1 and 1A-1D illustrate the general anatomy of the eye and an example surgical entry location for insertion of an ocular lens cutting device.
Figure 1A:
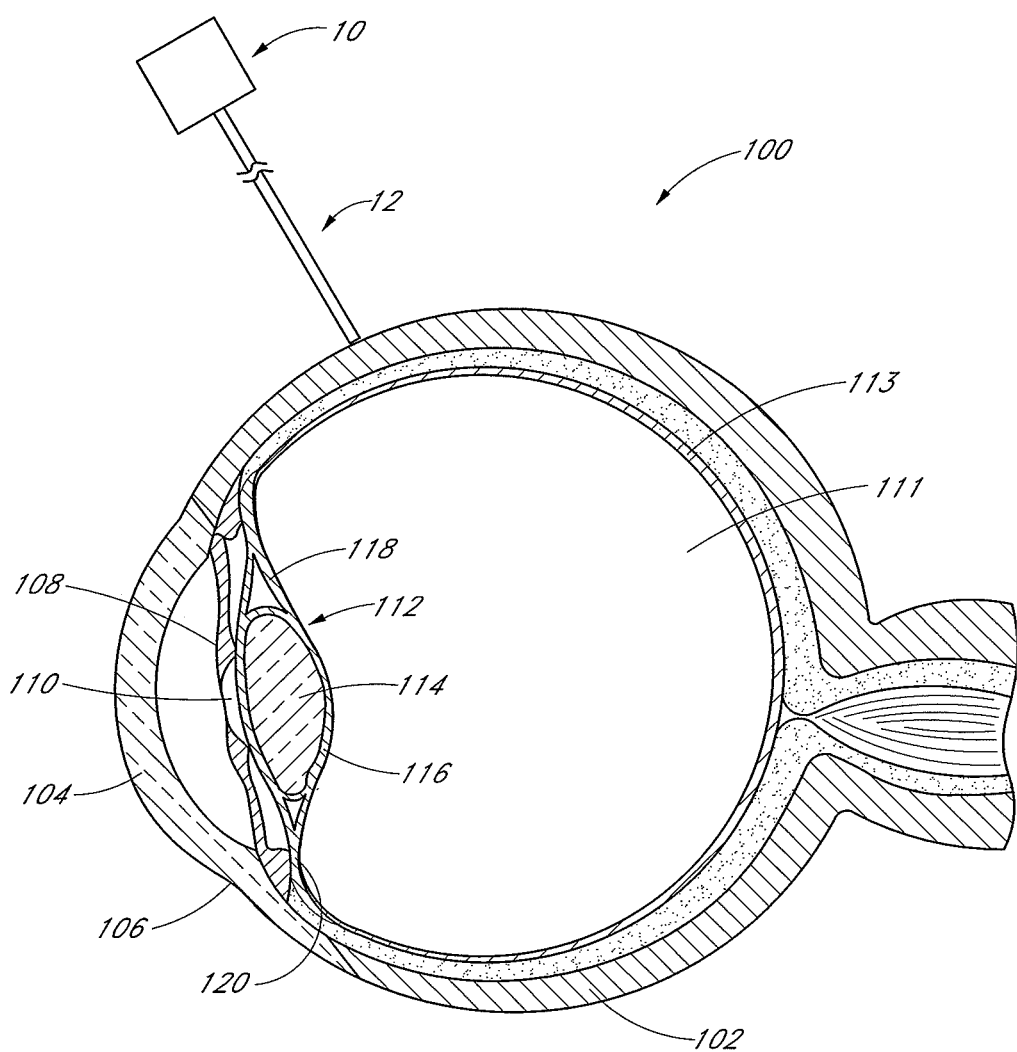
Figure 1B:
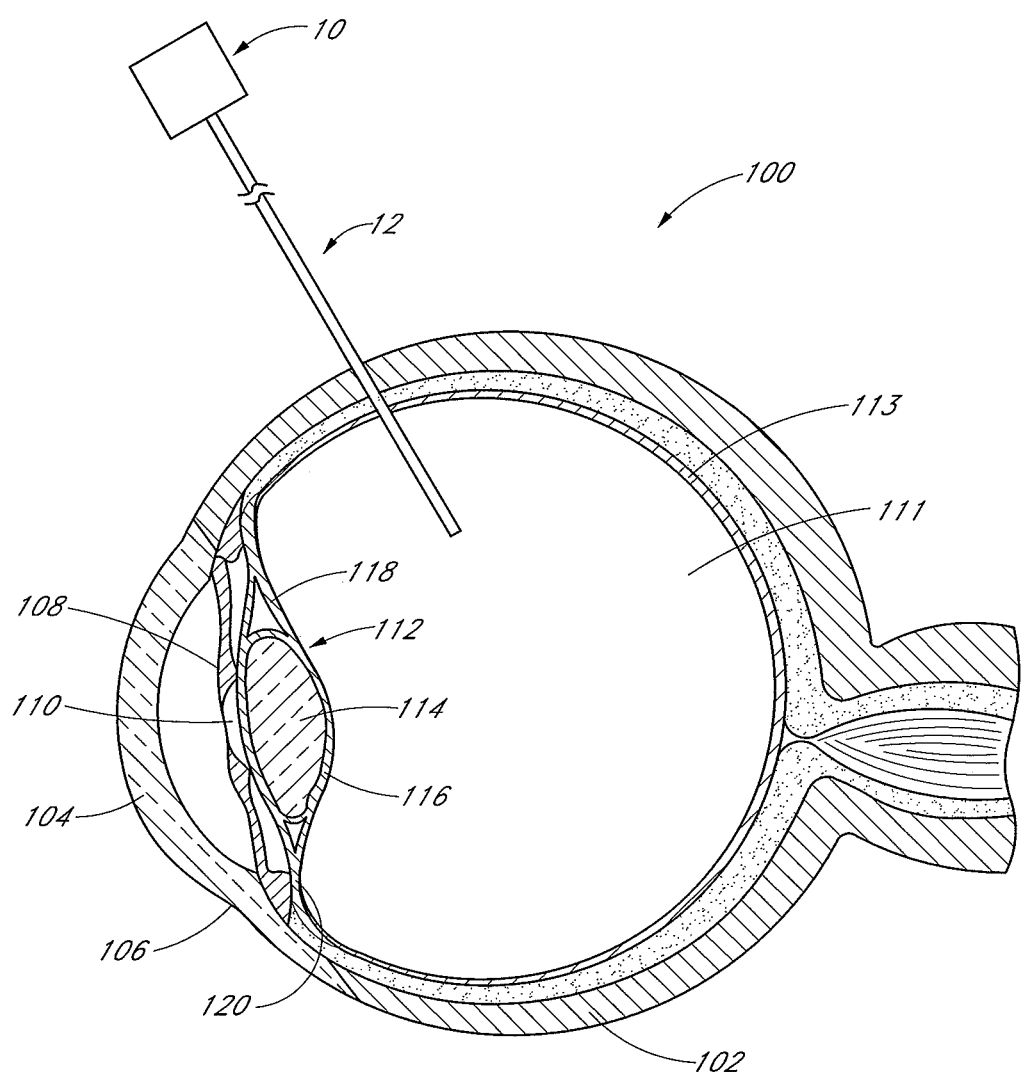

In some embodiments a cutting device can be used to cut and/or remove tissue, including eye tissue (for example, lens fragments, vitreous, or the like), such as during ophthalmic surgery. The cutting device can be used to break up tissue into smaller pieces for removal (for example, during cataract surgery). The device can also be used to remove tissue fragments from the surgical site. Although the cutting device is generally referred to herein as an ocular lens cutting device, and is primarily described with reference to removing tissue from the eye, such as during cataract surgery, it should be understood that the device and methods can be used in other fields and applications, such as removing cartilage, muscle, ligament, tendon, or bone tissue during surgery.

Referring to FIGS. 1 and 1A-1D, there is provided an illustration of a cross-section of the overall anatomy of an eye 100 and a schematic representation of an ocular lens cutting device 10. The outermost layer of the eye is made up of the sclera 102 and the cornea 104 which meet at the cornea-scleral junction or limbus 106. The iris 108 is visible through the transparent cornea 104 and forms the outer diameter of the pupil 110 or opening in the iris 108. Behind the iris 108 and pupil 110 is the lens 112. The lens 112 is made up of lens fibers 114 surrounded by the capsule 116 which is a thin transparent membrane. The lens 112 is held in place or suspended by the suspensory ligaments 118 of the lens which are connected to the ciliary body 120. The vitreous humor or body 111 is a clear gel that fills the space between the lens 112 and the retina 113 of the eye.

The lens 112 is a transparent, biconvex structure in the eye that, along with the cornea, helps to refract light to be focused on the retina 113 which is a light-sensitive tissue lining the inner surface of the eye 100. The lens, by changing shape, functions to change the focal distance of the eye so that it can focus on objects at various distances, thus allowing a sharp real image of the object of interest to be formed on the retina.

One of the most common ailments of the lens is cataracts. Cataracts results in opacity or cloudiness of the lens. While some are small and do not require any treatment, others may be large enough to block light and obstruct vision. Cataracts, as well as other ailments of the eye, may require surgery. For example, cataract surgery generally requires the removal and replacement of the lens.

Figure 1C:
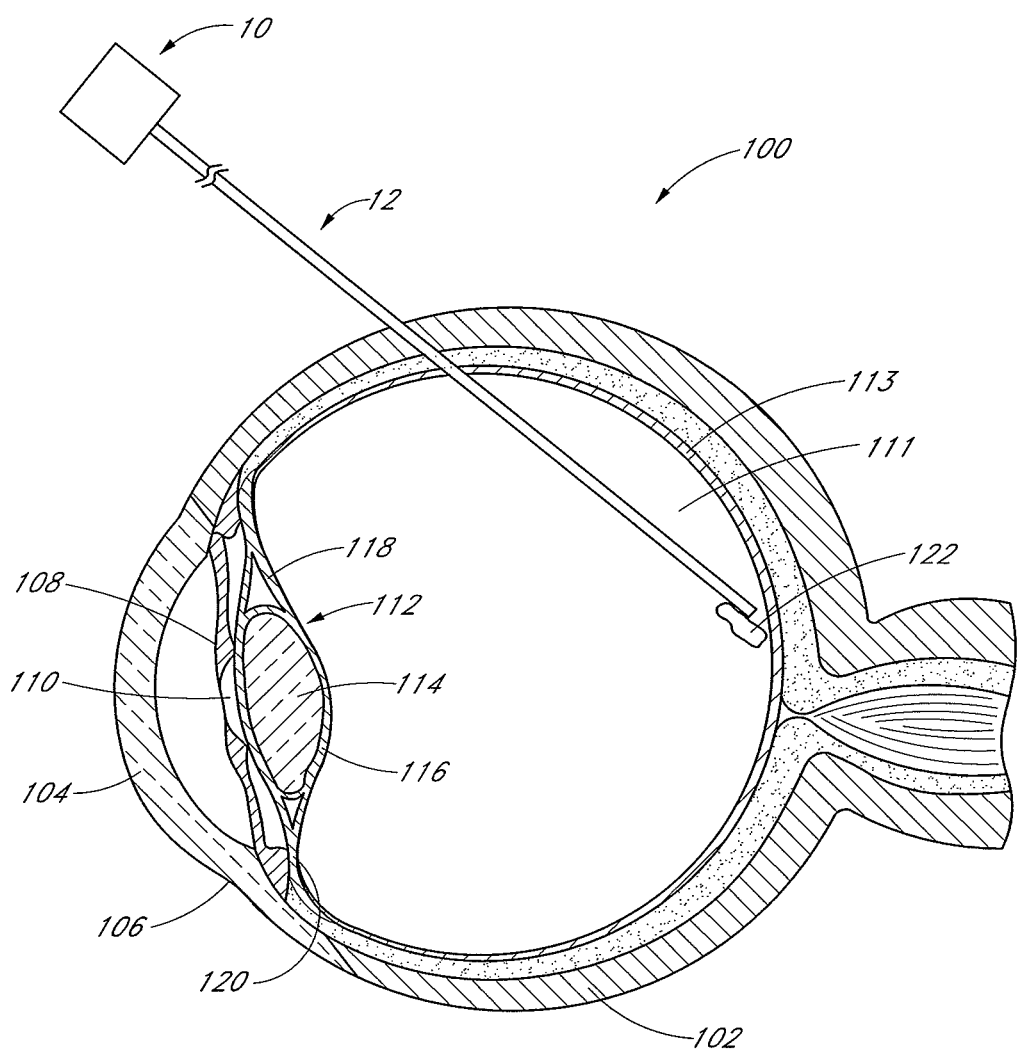
Figure 1D:
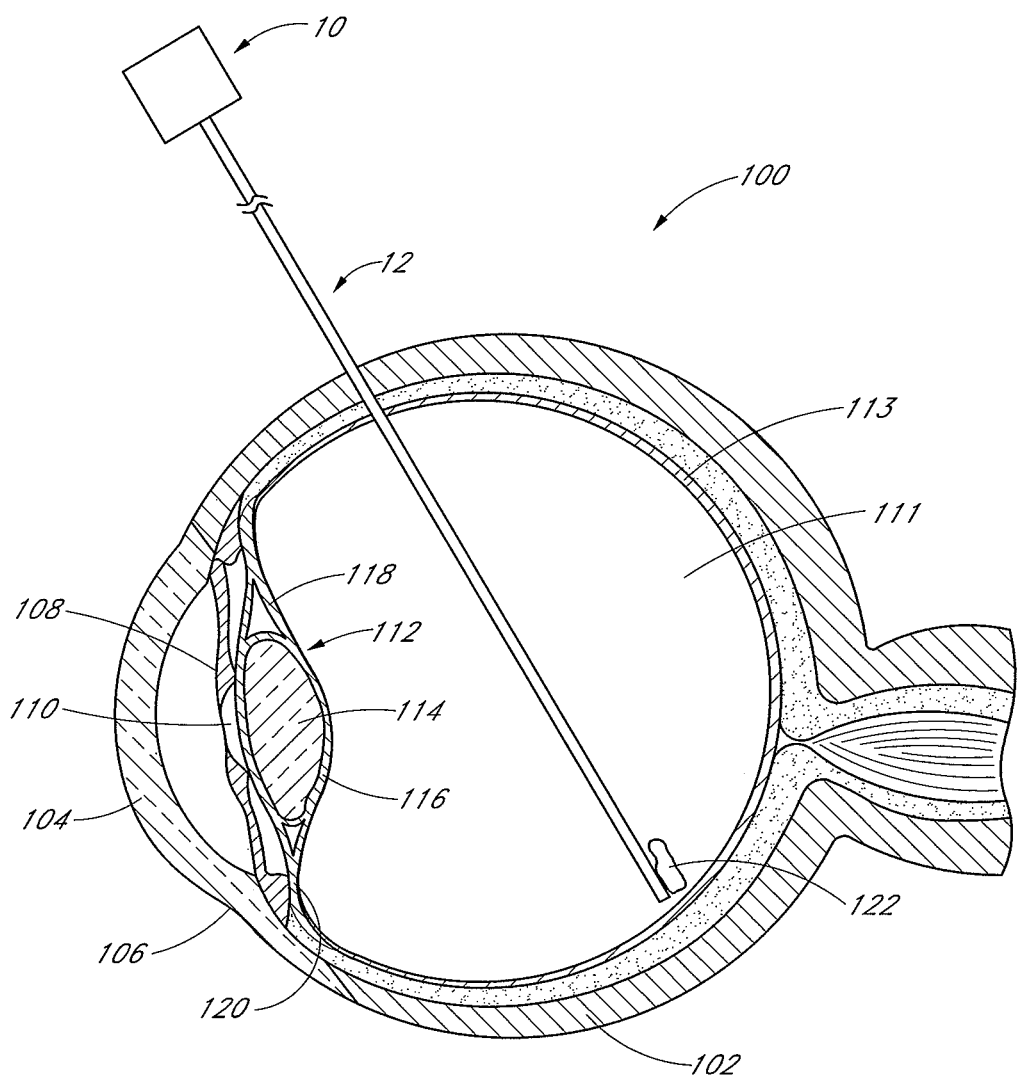

Still referring to FIGS. 1 and 1A-1D, an example insertion site of an ocular lens cutting device 10 is shown. An ocular lens cutting device can be used to remove tissue in the eye, such as the lens. In some embodiments, a distal end 12 of the cutting device, which may include a cutting tip, can be inserted through a small incision located at the corneo-scleral junction 106 and then though a hole in the lens capsule 116. Insertion of the cutting device 10 into the eye 100 can occur in one of many locations, including near the corneo-scleral junction 106, through the sclera 102, through the cornea 104, or at other locations of the eye. For example, as illustrated in FIGS. 1A-1D, the distal end 12 of the cutting device 10 can be inserted through a small incision located on an area of the sclera 102 that allows the distal end 12 of the cutting device to access the vitreous and/or the posterior portion of the eye without accessing the cornea-scleral junction 106 and puncturing the lens capsule 116. With the ocular lens cutting device 10 inserted into the eye 100, it can be powered on and used to morcellate the tissue of the lens fibers 114 or other eye tissue. For example, as illustrated in FIGS. 1C-1D, the cutting device 10 can be configured to access the posterior portion of the eye to retrieve lens fragments or particles 122 that have fallen into or dropped into the interior portion and/or posterior portion of the eye during a lens removal surgical procedure. A user of the cutting device 10 can use the distal end 12 to capture or draw in and hold the lens fragment 122 or other tissue while cutting into the lens fragment or tissue to break up the substance for suction into the internal lumen of the cutting device 10 and removal from the eye.

Figure 2:
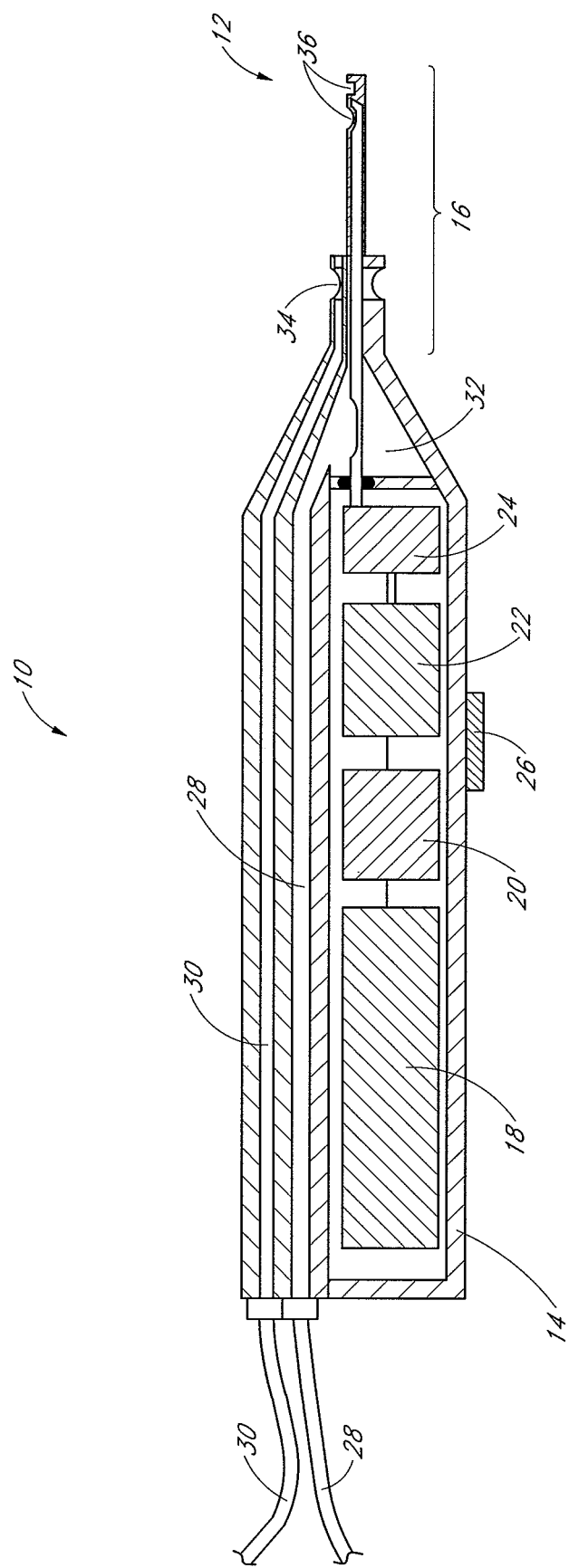
FIGS. 2 and 2A-2B are schematic cross-sectional views of an ocular lens cutting device.

Turning now to FIG. 2, a schematic representation of an ocular lens cutting device 10 is illustrated. As shown, the device can optionally be a handheld device. The ocular lens cutting device 10 can have an outer housing 14 and a working end 16. The working end 16 can have one or more features including a cutting feature, an aspiration feature, and an irrigation feature. In some embodiments, the working end 16 is at the distal end 12 of the device though other configurations are also possible. For example, in some embodiments, the working end 16 can be perpendicular to the rest of the outer housing 14 such that the device forms an "L" shape.

The housing 14 can encapsulate the internal components of the ocular lens cutting device 10 allowing the surgeon to grasp and manipulate the device during surgery. In some embodiments, the ocular lens cutting device 10 is configured for single-handed operation. The internal components can include a control/drive circuit 20 and a motor 22. In some embodiments, the device can include an internal power source 18, such as a battery. In other embodiments, the device can be connected to an external power source.

Figure 2A:
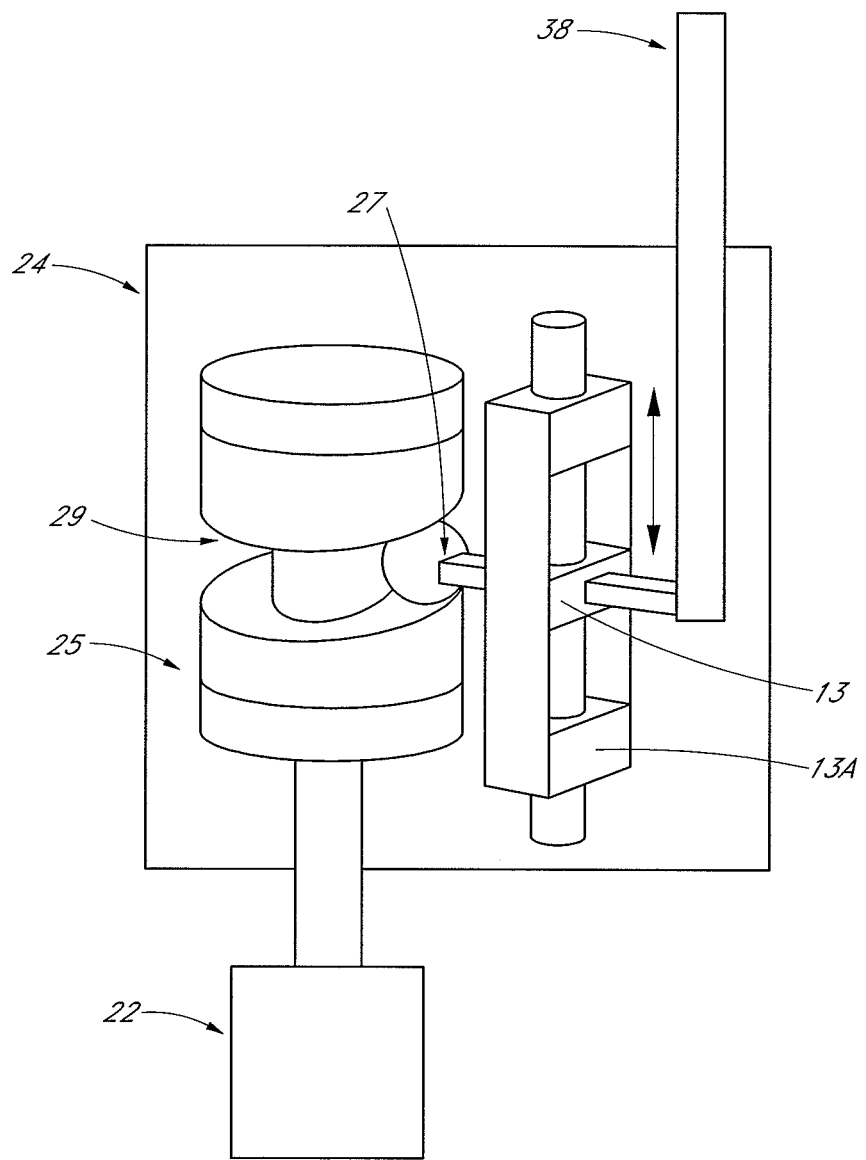
Figure 2B:
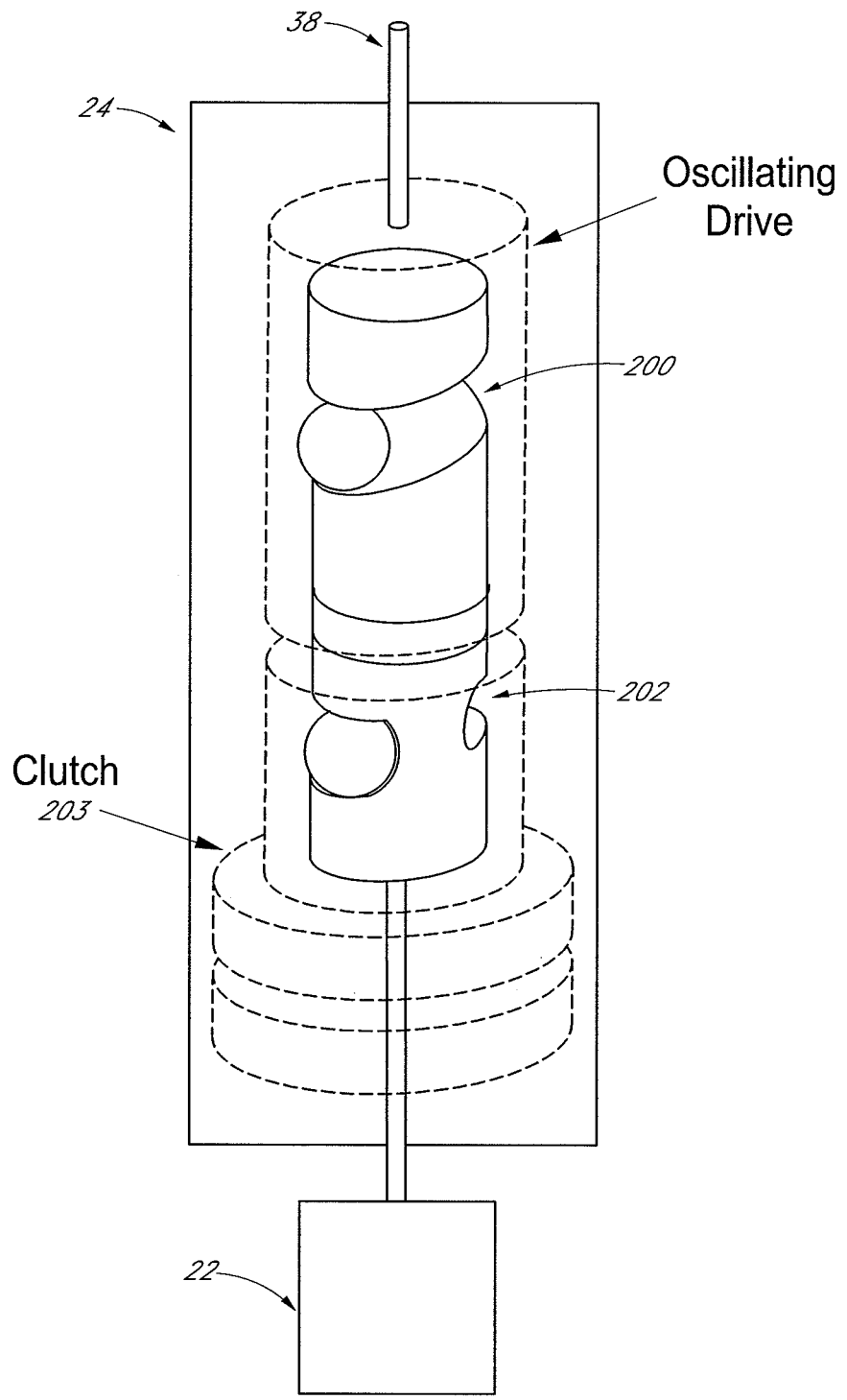

The device 10 may also include a gearbox 24. The gearbox 24 can be used to change or modify the output from the motor 22. For example, the gearbox 24 can transition a relatively higher speed and lower torque rotary motion to a lower speed yet higher torque motion (thus stronger force) for cutting hard tissues (for example, nucleus, cataract, cartilage). The gearbox 24 can advantageously increase the torque output of the motor 22 without requiring a high speed motor. As another example, the gearbox 24 can convert a rotary motion into a linear motion. For example, the gearbox 24 can comprise a ball configured to follow a sinusoidal groove to convert rotary motion of the motor into a reciprocating linear motion for the inner tube or sleeve 38 to move across the opening or port on the outer tube or sleeve 40 (illustrated in FIGS. 3-6). Alternatively, as illustrated in FIG. 2A, the ball can be substituted with a cam follower or a protrusion or other projection 27 that is configured to sit within and follow the sinusoidal groove 29 in cylindrical cam 25 to convert rotary motion into a reciprocating linear motion for the inner tube or sleeve 38 to move across the opening or port of the outer tube or sleeve 40 (illustrated in FIG. 2A). As illustrated in FIG. 2A, the follower 27 is coupled to a reciprocating slider 13 that is configured to slide within housing 13A. As the follower 27 follows the sinusoidal groove 29, the reciprocating slider 13 slides back and forth within the housing 13A. The slider 13 can be coupled to inner tube or sleeve 38 to cause the inner tube or sleeve 38 to move in a reciprocating linear motion within outer tube or sleeve 40. Other configurations of the foregoing are possible. Alternatively, the gearbox 24 can comprise a wobble plate coupled to a slider (not shown) configured to follow the movement of the wobble plate in order to convert rotary motion into linear reciprocating motion. As illustrated in FIG. 2B, the gearbox 24 may comprise any of the foregoing cam configurations to convert rotary motion into linear reciprocating motion, as illustrated by element 200, and additionally a clutch may be provided to advance and retract the inner tube or sleeve 38 from proximity of the opening or port 36B of the outer tube 40, as illustrated in FIGS. 3-6. Motor 22 may provide rotary motion in a first direction, causing the clutch 203 to retract the inner tube or sleeve 38 thereby ensuring the opening or port 36B of the outer tube 40 remains open when the cutting device has been turned off or deactivated. By allowing the opening of the outer tube to remain open when the cutting device is off, an aspiration level through the opening can be controlled by the surgeon. Maintaining port 36B open also prevents the possibility of having tissue trapped between inner tube 38 and outer tube 40 creating a danger of traction damage when the distal end 12 is retracted. Rotating motor 22 in a second direction, causes the clutch to advance the inner tube or sleeve 38 to be within proximity of the opening or port 36B of the outer tube 40 thereby allowing the inner tube or sleeve 38 to engage with the opening or port 36B of the outer tube 40 to cut tissue. The motor 22 and/or gearbox 24 can be used to effect rotary motion, circular or linear oscillation, and/or vibration. The motor 22 can also be a pneumatic drive mechanism that is known in the art such that gearbox 24 is not needed and the inner cutter is attached to the pneumatic drive mechanism and the reciprocating motion of the inner cutter is controlled by the pneumatic pulses.

Referring back to FIG. 2, the ocular lens cutting device 10 can have one or more inputs 26. The one or more inputs 26 can be used to control the ocular lens cutting device 10, including the actions of the working end 16. The control inputs 26 can comprise switches, buttons, touch-sensitive elements, and/or other input devices. For example, the input 26 can be a push button switch that turns on the motor 22 via the control/drive circuit 20 powered by the power source 18. The control/drive circuit 20 can then control the operation of the motor 22 to effect movement at the working end 16. In some embodiments, the control/drive circuit can comprise a circuit board and one or more electronic devices or components coupled to the circuit board.

The device 10 can include and/or be connected to an aspiration or vacuum line 28 and/or an irrigation line 30. In other embodiments, an aspiration or vacuum line 28 and/or an irrigation line 30 are optional because aspiration and/or irrigation and/or infusion can be performed by other cannulas inserted through optional ports inserted into the eye (for example, through the sclera). By removing the vacuum line 28 and/or the irrigation line 30, the device 10 can be reduced in size, cost, and/or complexity. In an embodiment, removal of the optional vacuum line 28 and/or irrigation line 30 can reduce strain on the user's hand because there can be no extra weight and/or pulling effect caused by a vacuum line or irrigation line hanging off the proximal end of the device 10. In some embodiments, the housing 14 can include an internal aspiration line 28 and/or irrigation line 30, as shown in FIG. 2. The housing 14 can also include an aspiration chamber 32. The aspiration chamber 32 can function as a reservoir of waste fluid for potential reflux purposes. An aspiration line 28 can be coupled to the aspiration chamber 32 to remove the broken-up pieces of tissue during operation of the ocular lens cutting device 10. In some embodiments, the vacuum/aspiration function provided by the aspiration chamber 32 and/or aspiration line 28 facilitates the grasping and holding of tissue fragments to improve the cutting and removal of tissue.

The aspiration line 28 and/or irrigation line 30 can be coupled to the working end 16 in order to allow for aspiration and/or irrigation during use. The working end 16 can include one or more apertures, openings, or ports 34, 36 through which a vacuum and/or irrigation fluid can be delivered to the surgical site.

The control inputs 26 can be used to toggle the power on and off, vary the cutting speed at the working end 16, toggle aspiration on and off, adjust aspiration levels, toggle irrigation on and off, and adjust irrigation levels. In some embodiments, a first control input 26 is used to power on and off the device 10 and a second control input 26 (not shown) is used to activate a feature at the working end 16. Device 10 may also be controlled by a foot controller (not shown) as is known.

Turning now to FIG. 3, a working end 16, according to some embodiments, will be described in more detail. The working end 16 can have various configurations and functions. As has been described, the working end 16 can include features such as a cutting tip, aspiration, and/or irrigation. FIG. 3 illustrates a working end 16 that combines both a cutting tip and continuous aspiration. The cutting tip can be configured to cut, emulsify, and/or remove tissue. The working end 16 can be used to remove the lens 112 of the eye 100 in part or in its entirety.

In some embodiments, the number of features on the working end 16 can be minimized in order to decrease the size of the working end 16. For example, the working end 16 can include a cutting tip and aspiration while irrigation can be provided by another device. Minimizing the size of the working end 16 can beneficially reduce the size of the working end 16 advanced into the eye. Certain small incisions in the eye do not require suturing to close the incision after the operation. For example, the working end 16 can be approximately 23-30 gauge or 25-30 gauge. The working end 16 according to certain embodiments can be advanced through a small incision that generally does require suturing after the surgical procedure.

As shown, the working end 16 comprises a two-part construction, including an inner tube or sleeve 38 that fits within and can move with respect to an outer tube or sleeve 40. This movement creates a cutting motion, similar to scissors, which can be used to cut the lens 112 into fragments 112A. Still further, the working end 16 can be connected to a remote vacuum source that creates a vacuum at the working end 16. The vacuum can assist in holding the lens 112 to the working end 16 (commonly referred to as purchase). The vacuum can also draw a portion of the lens 112 into the working end 16 to cut the lens into fragments 112A and aspirate the cut fragments 112A from the working end 16 through the device 10.

The cutting and aspiration functions of the working end 16 will now be described in more detail. After the ocular lens cutting device 10 has been placed within the eye in the desired position, the vacuum can be turned on, such as through the input 26 shown in FIG. 2. With the aspiration or vacuum turned on, the device 10 can secure itself to the tissue desired to be cut and/or removed, such as the lens 112. This is done through the suction force caused by the aspiration line with the suction experienced at holes, openings or ports 36A and 36B. The inner tube 38 and outer tube 40 can be hollow, or substantially hollow to allow aspiration flow through the tubes 38, 40. The tubes can be tubular, cylindrical members or other shapes. In some embodiments, the distal end 44 of the inner tube 38 can be open to allow flow therethrough, such that a vacuum can create a suction flow through the inner tube 38. In an embodiment, the distal end of the outer tube 40 is closed because aspiration at the distal tip of the outer tube 40 may cause safety issues in situations when the surgeon cannot see the distal end. In an embodiment, the distal end of the outer tube 40 is open to allow aspiration therethrough. Other configurations are also possible such that a vacuum is created at the distal end of the working end and/or at holes 36A and 36B. Though two holes 36A, 36B are shown, the device 10 may include more or less holes 36. In addition, the holes 36 can have many different shapes such as to best utilize the cutting and aspiration features, which may depend on many factors including the tissue to be cut.

Once a vacuum has been created and the working end 16 is in place next to the tissue 112 to be cut, the inner tube 38 can be moved with respect to the outer tube 40 to create a cutting motion. As can be seen with reference to FIGS. 3-6, the inner tube and outer tube can cut tissue as the inner tube is moved linearly, i.e. pushed and pulled. The tissue can become trapped between the two tubes and then cut and fragmented as a result.

FIGS. 3 and 4 illustrate a push stroke, where the inner tube 38 moves towards the distal end 12 of the outer tube 40. The cutting action can occur between the hole, opening, or port 44 of the inner tube and the circumferential edge of the hole, opening or port 36B. The portion of the lens 112, or other tissue, that has been drawn into the hole 36B is trapped between the two tubes and can be cut into a fragment 112A. The fragment 112A can then be drawn into the working end 16 by suction, such that the fragment 112A is removed from the working end 16 and ultimately removed from the device 10.

Figure 5:
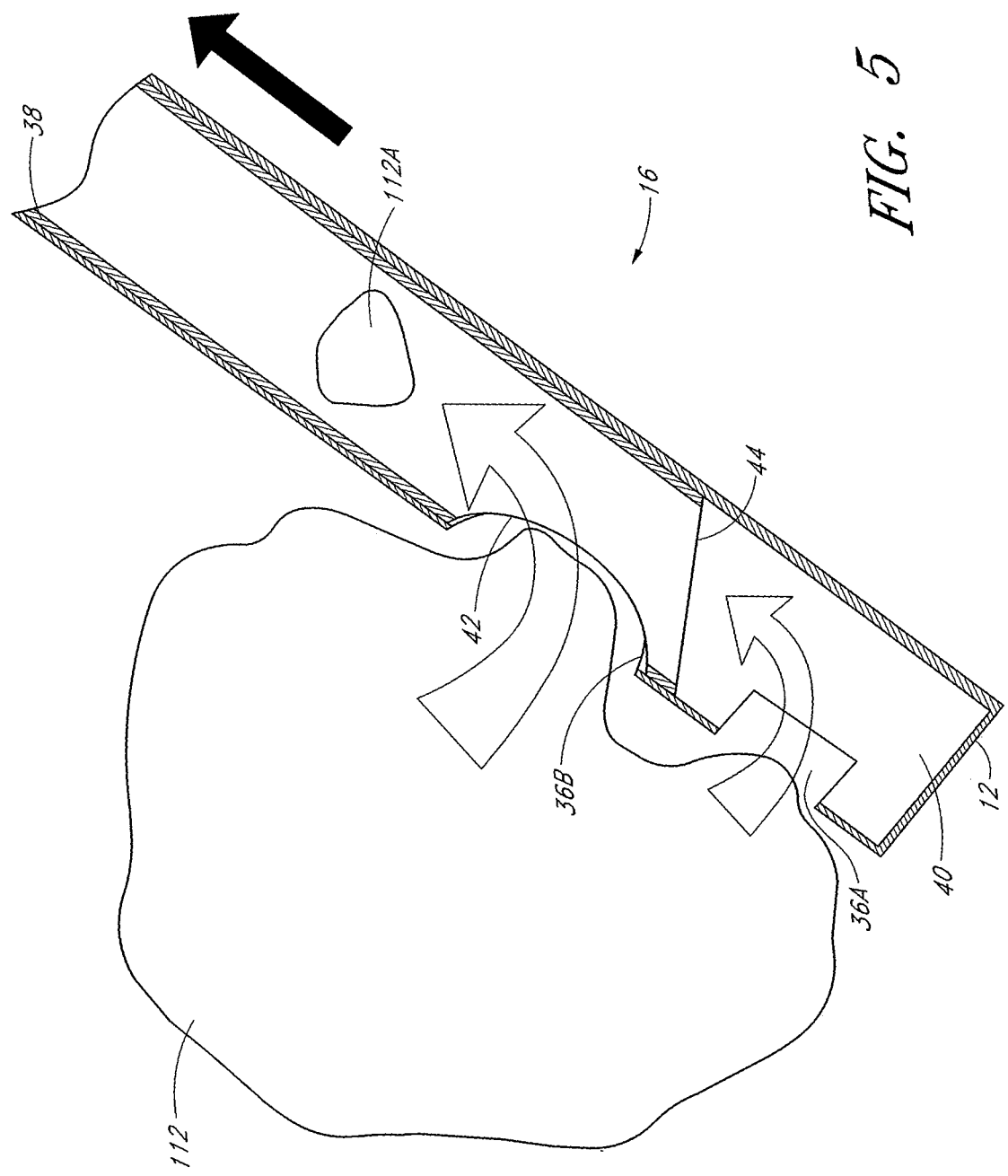
Figure 6:
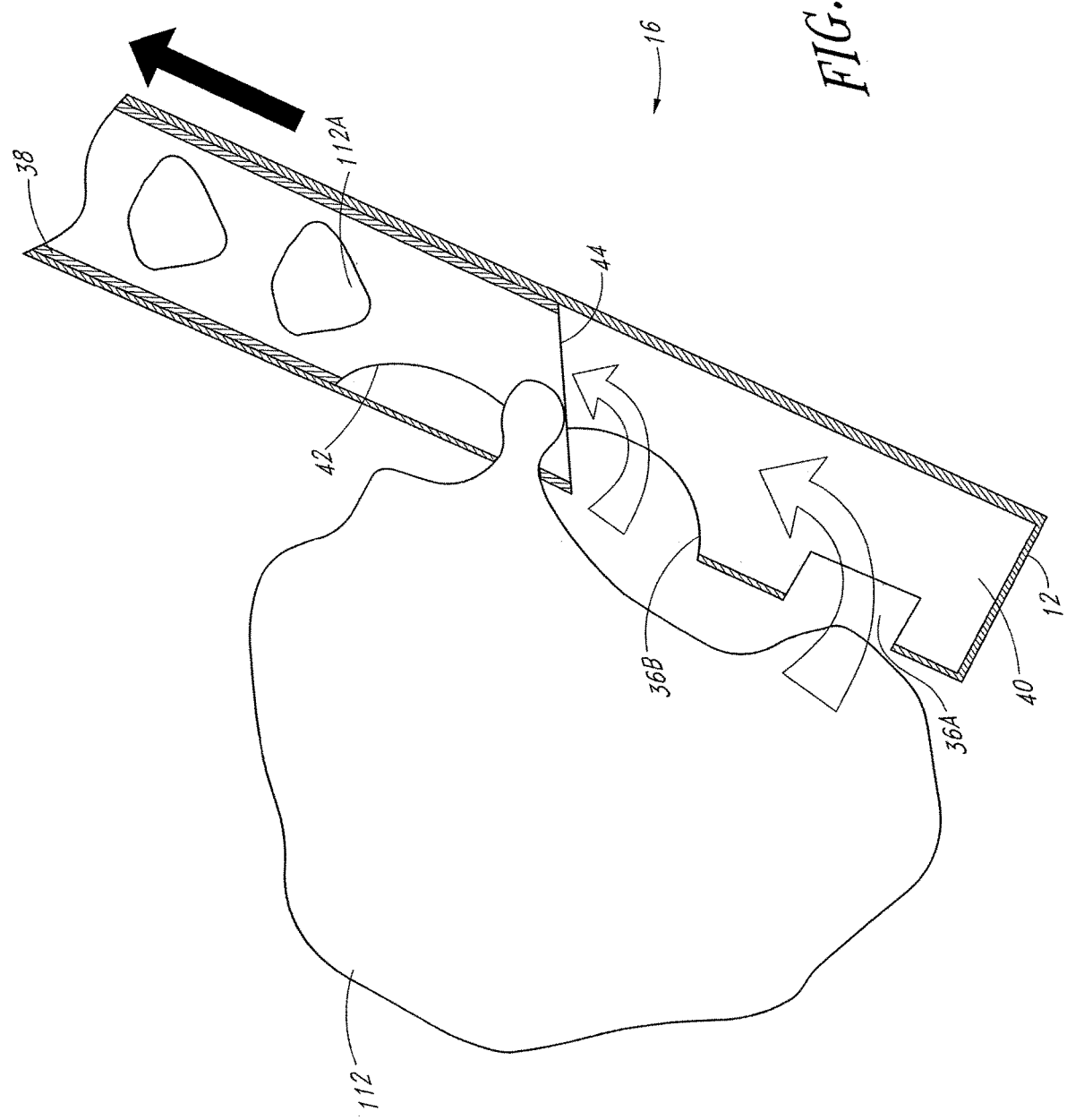

Looking now to FIGS. 5 and 6, the pull stroke is shown. As before, the hole 36B can draw another portion of the lens, or other tissue, into the hole 36B. This portion can then be cut into a fragment of the lens 112A and removed as the hole, opening or port 42 of the inner tube 38 acts with the proximal end of the hole 36B to cut tissue. While the inner tube 38 is illustrated with port 42, the inner tube 38 can be constructed without such a port and therefore will only cut tissue on the push or extending stroke. This will allow outer port 36B to be completely blocked by inner tube 38 and may be desirable for particular applications. In addition, some known scheme to bias inner cutter towards outer port 36B may be required to ensure a reliable complete severing cut of tissue 112. Many such biasing schemes are known to those skilled in the art.

FIGS. 3 and 5 represent the beginning and/or ending of a cutting stroke, while FIGS. 4 and 6 are representative of a position during a cutting stroke. It should be understood that the process can cycle through many cutting strokes. In other words, after FIG. 6, the process can cycle back to the position shown in FIG. 3 and then proceed through one or more additional cutting strokes. In addition, the process can start or finish with the inner tube 38 at any position within the outer tube 40, such as any of the positions shown in FIGS. 3-6, as well as positions in-between.

In the illustrated embodiment of FIGS. 3-6, the inner tube 38 has two separate cutting edges in holes 42 and 44. The hole 42 can have one cutting edge that extends around the entire hole. In other embodiments, the hole 42 can have separate cutting edges, such as a distal cutting edge and a proximal cutting edges. The other holes 36, 44 can similarly have one or more cutting edges. The working end 16 can also have different configurations. For example, instead of the inner tube moving linearly with respect to the outer tube, the inner tube can move radially, such as to rotate or partially rotate about the axis of the inner tube and outer tube. This would move the cutting action from the distal and proximal ends of the hole 36B to the radial sides. The cutting configuration can also take other shapes, sizes, or configurations other than the substantially circular elliptical configurations shown. In an embodiment, the axial length of the opening 36B (the length along the length of the outer tube 40) can range from about 0.30 inches to about 0.1 inches. In an embodiment, the axial length of the opening 42 (the length along the length of the inner tube 38) can range from about 0.020 inches to about 0.1 inches. For example, the opening 42 can have a smaller or larger axial length or size than the opening 36B. It can be advantageous to configure opening 42 to have a different size than opening 36B to enable more efficient cutting and/or to prevent clogging of the inner tube. By configuring the opening 42 to be smaller than the opening 36B, the cutting device can be configured to cut off smaller tissue pieces, which can help prevent clogging of the inner tube. Further, by configuring the opening 32 to be smaller than opening 36B, the device 10 can be configured to assist in holding a larger portion of the lens 112 while a smaller portion of the lens 112 is cut by the inner tube 38, which may allow for simultaneous holding and cutting. For example, the ratio of the axial length of opening 42 to the axial length of opening 36B can be about 1:2, and in other embodiments, the ratio can be about 1:3, 1:4, 1:5, 3:4, 4:5, 9:10, or the like. In still other embodiments, the ratio can be about 2:1, 3:1, 4:1, 5:1, 4:3, 5:4, 10:9, or the like. If clogging does occur, the device 10 can be configured to reverse the flow, or to cause reflux, in the lumen of the inner tube by turning off the vacuum and injecting fluid into the inner lumen. The holes 36B, 42, and/or 44 can have serrated edges, beveled edges, or points. In some embodiments, at least a portion of the perimeter of the hole is curved or arcuate. In addition, though the inner tube 38 is shown as a cylinder with holes 42 and 44, alternative configurations are also possible such as an elongate member having a cutting loop at the distal end to replace or as part of the inner tube 38 to function in a similar manner to the cutting edges at holes 44 and 42.

In some embodiments, one or more of the holes 36A, 36B, 42 and/or 44 can be generally circular or elliptical, square, rectangular, triangular, diamond, pentagonal, or other shapes. In addition, the holes can be a combination of shapes such as the two or three or more connected generally circular or elliptical cutouts shown in FIGS. 7-9. In an embodiment, the openings 36B and 42 can comprise multiple openings to allow for more cutting surfaces and increased cutting efficiency.

As has been mentioned, suction can be used to draw tissue into the device. This can serve various purposes. Suction can be used to hold the tissue in place, for example, within the cutter such that a section of the tissue is drawn into the hole 36B, to be cut by the cooperating edges of hole 36B and either hole 42 or hole 44. Suction can also hold the tissue in place next to the device.

Advantageously, the cutting device 10 has two or more holes at the working end 16, with a suction force to act on the tissue. As illustrated in FIGS. 3-6, each hole can serve a separate primary purpose, though other configurations are also possible. Hole 36A can be used primarily to hold or purchase the tissue to the device, for example, the lens fragment 112. In an embodiment, the axial length of the opening 36A can range between about 0.007 inches to about 0.025 inches. This can help position the lens 112 relative to the cutting device 10 in the desired location for removing tissue via outer port 36B. The second hole 36B can be used to draw the tissue into the device 10 to be cut and removed via outer port 36B. In this way, one hole, here 36A, can be used to hold the tissue, or secure the device to the tissue, while the other hole 36B is cutting tissue and drawing the tissue fragments into the device for removal. In an embodiment, opening 36A can comprise a plurality of smaller openings clustered together, which can be advantageous in holding the tissue to the working end 16 without drawing tissue inside outer tube 40 while the second opening 36B is used to cut and breakdown tissue for removal from the eye.

The suction force at hole 36B is constantly changing because the inner tube 38 is moving with respect to, and sometimes obstructing the hole 36B (in an embodiment, this is only true if tube 38 does not have opening 42 because with opening 42 there is generally a constant aspiration at 36B). This movement changes or varies the size of the hole 36B and the area available for suction with the tissue to be cut 112. In fact, it can be considered that the inner tube 38 effectively divides hole 36B into two separate holes when the distal end of the inner tube is within the hole 36B. This also changes the amount of suction that can be applied to the tissue.

At the same time, as illustrated, the hole 36A remains unchanged in exposed surface area as the inner tube 38 does not obstruct or interact with the hole 36A. At times during the process, this allows more of the suction to be applied at hole 36A, thereby retaining the lens fragment 112, or the tissue to be cut in position with respect to the working end 16. Such a configuration allows for the correct position of the working end to be maintained by the continuous aspiration at opening 36A, while also allowing the cutting and removal of the desired tissue at opening 36B.

In FIGS. 3-6, curved arrows are used to represent the relative size or level of vacuum created at each particular hole 36A, 36B at particular times during the cutting and removing process. As can be seen, the level of vacuum can be affected by the relative position of the inner and outer tubes as they are moved to cut tissue. In essence, in some positions, the inner tube blocks or reduces the size of the hole 36B. This can have the effect of reducing suction at hole 36B, while increasing suction at hole 36A.

In the beginning and/or ending of a cutting stroke shown in FIGS. 3 and 5, the hole 36B is unobstructed by the inner tube 38. This allows for a large suction force to be experienced at hole 36B. A suction force can also be experienced at the hole 36A. The size of the relative suction forces at holes 36A and 36B can be a result of many factors, for example, relative hole size, proximity to the suction source, etc. As shown in FIGS. 4 and 6, during a cutting stroke part of the inner tube 38 can block part of the hole 36B. This can result in a decrease in the total suction force at the hole 36B and an increase in total suction force at hole 36A.

Other configurations are also possible. For example, each hole 36A and 36B could have a dedicated aspiration or vacuum line. In addition, an additional channel could be added that extends only through the outer tube 40 and not through the inner tube 38. In addition, the inner and outer tubes can have different outer diameters or different outer shapes to create additional space or channels for the vacuum.

A method of using an ocular cutting device during surgery of the eye can comprise one or more of the following steps. Advancing a distal end of an ocular cutting device into a surgical site within the eye. The ocular cutting device can have an outer tube having first and second openings at the distal end, the first opening having a first cutting edge; an inner tube having a third opening with a second cutting edge; and a aspiration line configured to apply a vacuum to the distal end of the ocular cutting device at the first and second openings. Applying a vacuum to the distal end of the ocular cutting device at the first and second openings. Grasping a lens of the eye with the suction from the vacuum at the first and second openings on the ocular cutting device. Drawing a first portion of the lens into the first opening in the outer tube. Moving the inner tube with respect to the outer tube such that at the first opening the first portion of the lens drawn into the first opening is cut, creating a lens fragment while at the second opening, the lens remains attached to the ocular cutting device. Removing the lens fragment from the surgical site through suction and through the outer tube.

A method according to some embodiments may also include the following additional steps. Wherein moving the inner tube comprises moving in a linear manner with respect to the outer tube. In another embodiment, the inner tube can be configured move in a rotational manner with respect to the outer tube. In still another embodiment, the inner tube can be configured to move in both a rotational manner and a linear manner with respect to the outer tube. In embodiments where the inner tube is configured for rotational movement, the inner tube can be configured to perform complete rotations and/or the inner tube can be configured to perform partial rotations, for example, rotating 90 degrees in one direction and then returning to the starting position and then rotating 90 degrees in a second direction. The degree of partial rotation can be any degree of rotation between 0 degrees and 360 degrees, for example, 45 degrees, 180 degrees, or the like. Drawing a second portion of the lens 112 into the first opening 36B in the outer tube 40 and moving the inner tube 38 with respect to the outer tube 40 such that at, the first opening 36B, the second portion of the lens 112 is drawn into the first opening 36B is cut, creating a lens fragment while at the second opening 36A, the lens remains attached to the ocular cutting device. Wherein the inner tube 38 can further comprise a lumen such that removing the lens fragment from the surgical site through suction. Wherein moving the inner tube 38 with respect to the outer tube 40 may further comprise moving the first and second cutting edges 406, 404 to cut the first portion of the lens. Wherein the inner tube 38 can further comprise a fourth opening 44 and a third cutting edge 402, and moving the inner tube 38 with respect to the outer tube 40 further comprises moving the first and third cutting edges 406, 402 to cut the first portion of the lens 112.

The ocular cutting device 10 disclosed herein is ideally suited for many surgical procedures. One example, is where the lens capsule 116 has been ruptured causing the lens 112 to fall onto the retina 113. In such a procedure the ocular cutting device 10 can be used to pick up the lens 112 from off the retina 113 with the suction force at one or more holes 36. The ocular cutting device 10 can then cut and remove the lens in fragments as has been discussed. The ocular cutting device 10 can prevent lens fragments from falling back onto the retina or from being projected onto the retina. In addition, the suction force from the ocular cutting device 10 can prevent the lens from falling onto the retina.

In some procedures, the ocular cutting device 10 can be used as the primary cutting and removal tool for the operation. In some procedures, the ocular cutting device 10 can be used with or in addition to other cutting tools. For example, where the lens capsule 116 has been ruptured and the lens has fallen onto the retina, the initial removal of the lens could have been performed by another device that caused the capsule 116 to rupture. In addition, the vitreous body 111 may be removed by another device prior to the ocular cutting device 10 picking up the lens 112 from off the retina 113. In addition, a separate irrigation device can be used to inject balanced salt solution (BSS) into the eye in order to maintain the proper intraocular pressure (IOP).

In some embodiments, an instrument can remove tissue from the eye while simultaneously holding the tissue. The instrument can consist of a linear oscillating drive mechanism contained within a body, a hollow tube or outer lumen, sealed at the distal end with two closely spaced ports at the distal tip, a second hollow tube, or inner lumen, with a section of material removed near the distal tip to create a strip with edges on both the upper and lower side with respect to the longitudinal axis. The outer lumen can be rigidly attached to an instrument body with the inner lumen located concentrically within the outer lumen and attached to the drive mechanism.

Figure 6A:
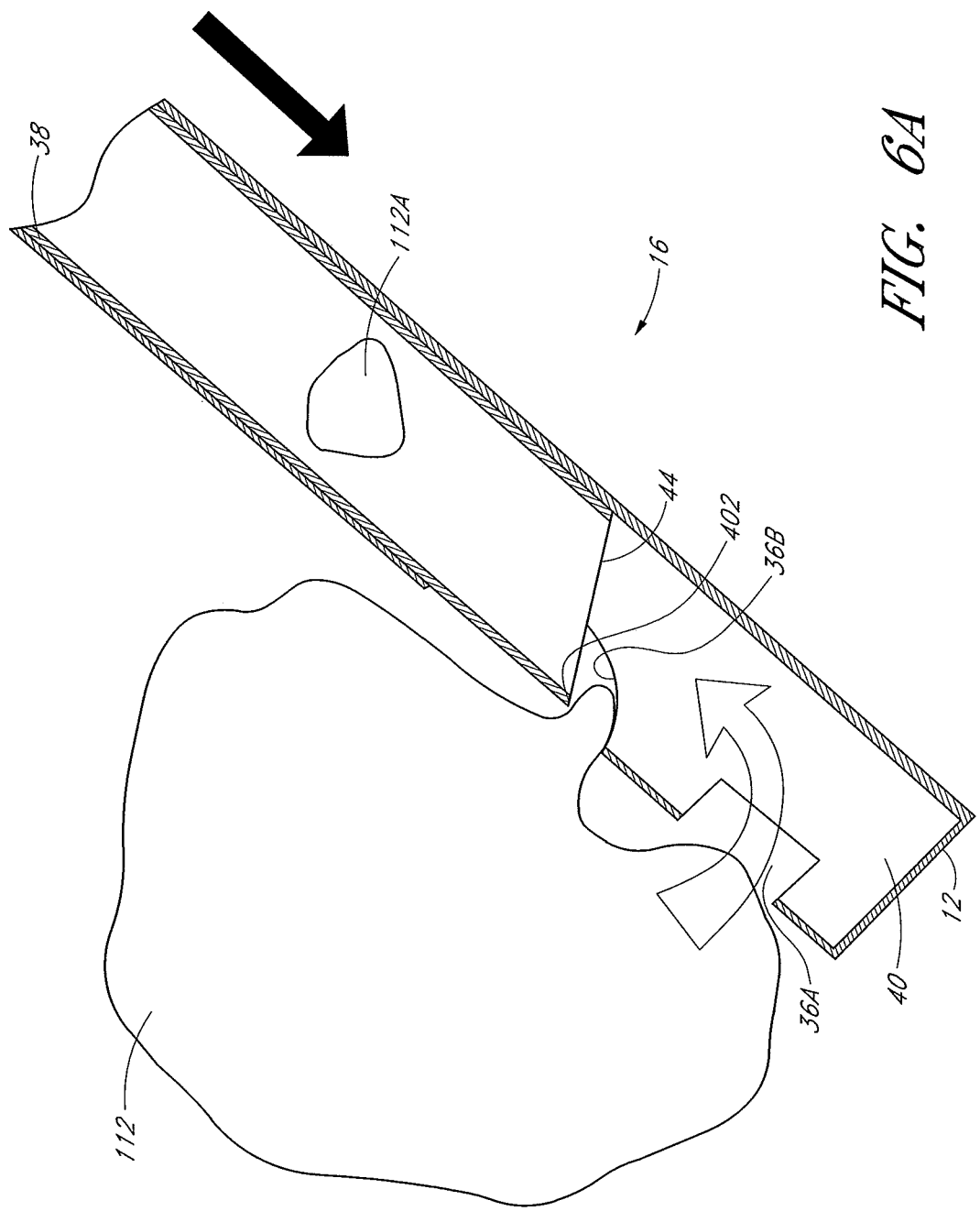

To cut tissue the inner lumen is reciprocated within the outer lumen creating a shearing action across only one of the distal ports, for example, the cutting port, on both the up and down stroke utilizing both edges of the distal strip. For example, in an embodiment, as illustrated in FIG. 4, the inner tube 38 not only comprises a cutting edge 406 along the entire perimeter of opening 36B but also comprises a cutting edge 402 at the distal end of the inner tube 38 and at opening 44. The cutting edge 402 at the distal end of the inner tube 38, and the cutting edge 406 along the opening 36B, can both be configured to cut tissue on down strokes as the inner tube moves toward the distal end 12 of the cutting device while the cutting edge 404 along the opening 36B can be configured to cut tissue on up strokes as the inner tube moves away from the distal end 12 of the cutting device. In other embodiments, as illustrated in FIG. 6A, the inner tube 38 is configured to cut tissue 112 only in a down stroke (or push stroke) towards the distal end 12 of the device 10. The second port closest to the tip of the outer lumen, i.e. the holding port, holds the tissue so that the reciprocating action of the inner lumen will prevent tissue from falling away from the tip. The inner and outer lumen has a fluidic connection to a vacuum source able to generate negative pressure to draw and retain tissue at the cutting and holding ports. Current instrumentation for removing lens material requires bimanual manipulation to hold fragments close to the port for removal. The holding port 36A may reduce or eliminate the need for bimanual manipulation. At least some of the devices disclosed herein can perform multiple functions to reduce instruments required, and surgery complexity. This can result in faster surgery and less risk to patients.

In some embodiments, the cutting port can be larger in size and closer to the instrument body than the second holding port. The outer lumen can be rigidly fixed to the body of the instrument with an inner lumen attached to a mechanical mechanism for providing reciprocating motion located within the instrument body. The inner lumen can also have a section of material removed at the distal end so as to leave a thin lateral strip with two cutting edges to reciprocate across the cutting port and create a shearing action at both upper and lower edges of the port. A vacuum source can be connected to the inner lumen to draw in the material so that it may be sheared.

Figure 6B:
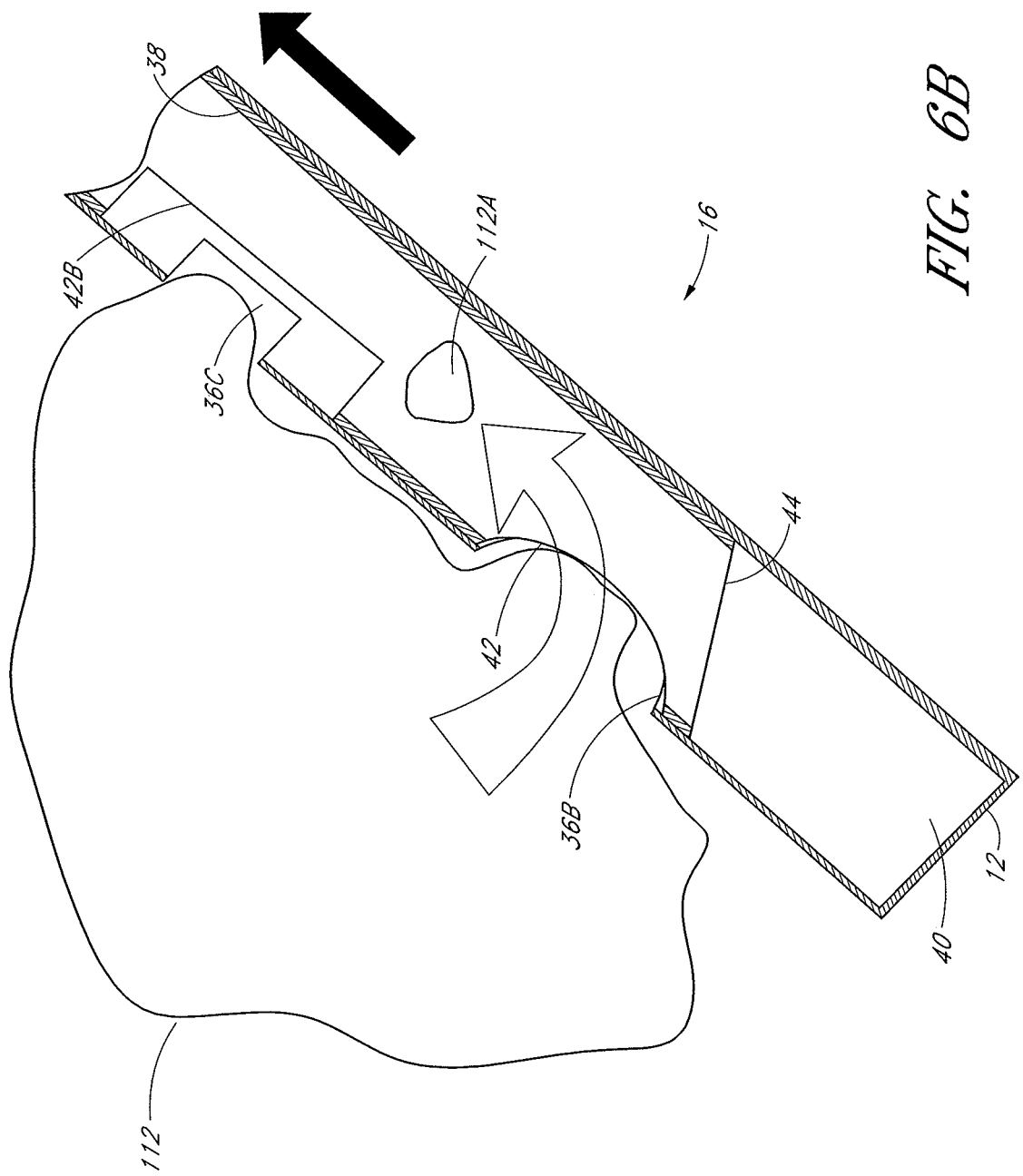

In some embodiments, as illustrated in FIG. 6B, the holding port 36C is located proximally from the cutting port 36B. The inner lumen can then have a large section 42B removed in order to accommodate the holding port 36C. In some embodiments, the strip at the distal end of the inner lumen can be angled with respect to the lateral direction to create a progressive shearing action. In some embodiments, the inner lumen includes an axially oriented cutting strip driven by an oscillating rotational mechanism or a fully rotational mechanism across the cutting port. The axially oriented cutting strip can also be angled to create a progressive shearing action. In some embodiments the holding port can be formed by a series of small holes creating a mesh, or by one than one hole.

Figure 7A:
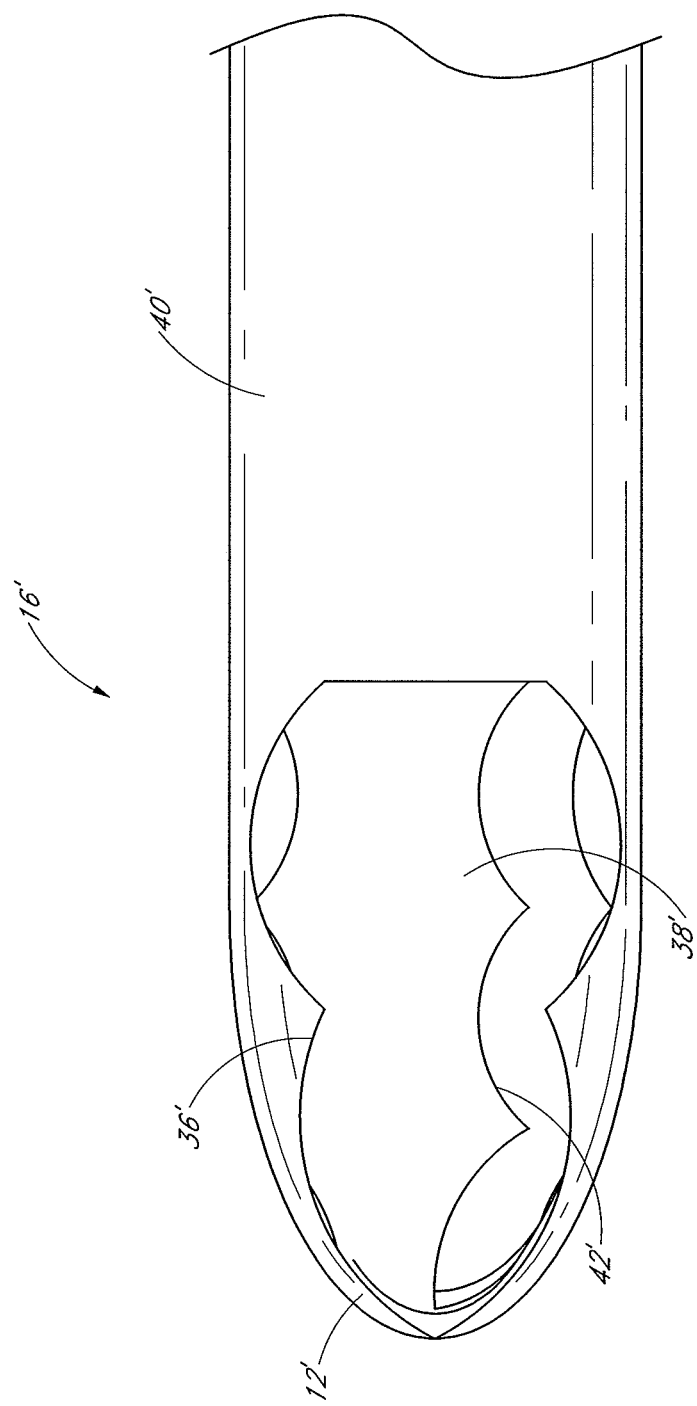
FIG. 7A shows the distal end of the ocular lens cutting device of FIG. 7 in a different position.
Figure 8:
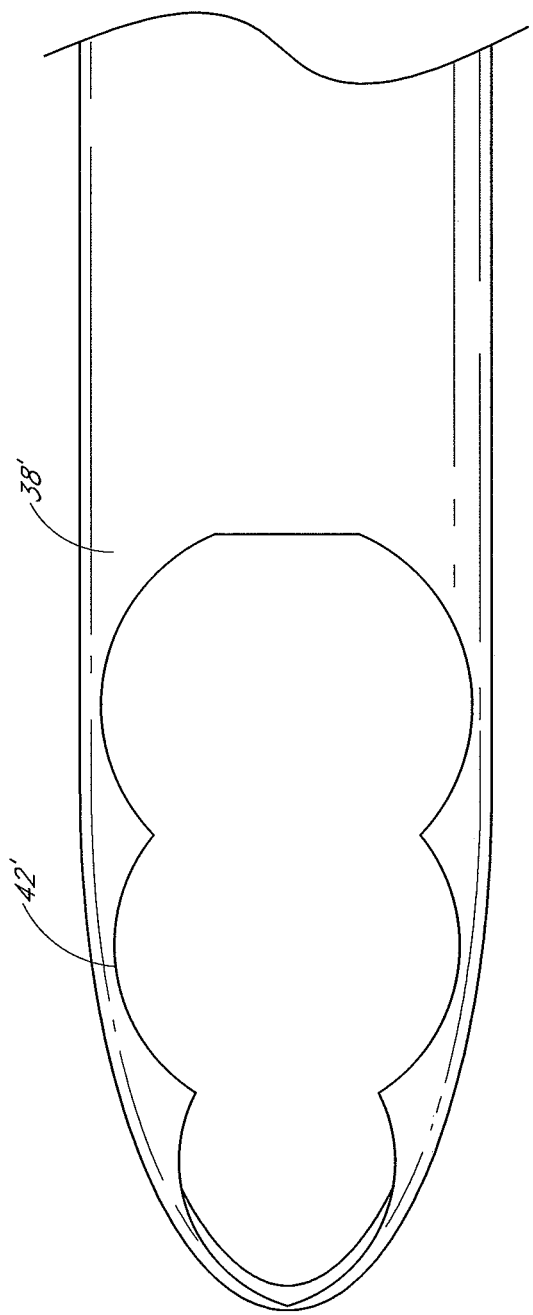
FIG. 8 illustrates an inner tube of the distal end of the ocular lens cutting device of FIG. 7.
Figure 9:
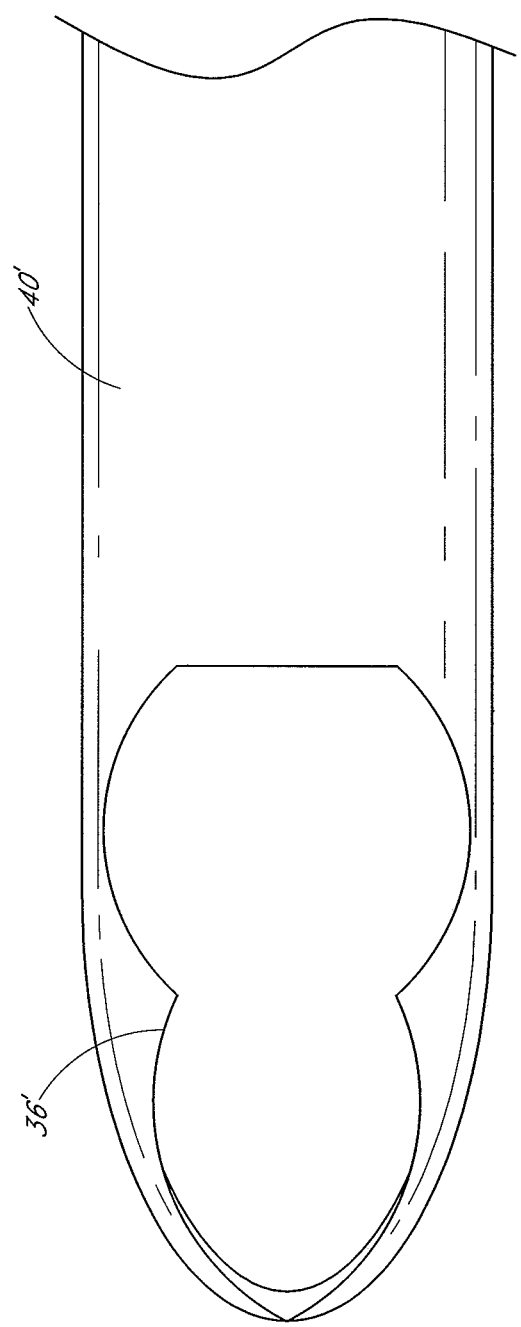
FIG. 9 shows an outer tube of the distal end of the ocular lens cutting device of FIG. 7.

Turning now to FIGS. 7-9, an alternative cutting configuration is illustrated. FIGS. 7 and 7A show the assembled cutting device while FIG. 8 illustrates the inner tube 38' and FIG. 9 shows the outer tube 40'. The illustrated cutting tip has a tubular outer cutting member 40' and an inner cutting member 38' positioned concentrically within the tubular outer cutting member 40'. The holes 42' and 36' can move with respect to one another such as by a rotating or a linear movement of the inner tube 38' or by a rotating or a linear movement of the outer tube 42'. In an embodiment, the opening 42' can comprise a cutting edge along the entire perimeter, or a portion of the perimeter, of the opening 42'. In embodiment, the opening 36' can comprise a cutting edge along the entire perimeter, or a portion of the perimeter, of the opening 36'. In an embodiment, the openings 42' and 36' can both comprise cutting edges along the entire perimeter, or a portion of the perimeter, of the openings 42' and 36'. In some embodiments, both the inner and the outer tube can move to create the cutting motion.

Preferably, the inner or outer tube can be rotated with respect to the other in one direction or in alternating directions to cause a cutting movement. In one embodiment, the tubular outer cutting member 40' remains stationary as the inner cutting member 38' rotates within the tubular outer cutting member 40'. In other embodiments, the outer cutting member 40' moves with respect to the inner cutting member 38'. In still other embodiments, both the outer cutting member 40' and the inner cutting member 38' rotate in opposite directions. Alternatively, either or both of the inner tube and the outer tube can move linearly in a push and pull fashion. This can cause a cutting movement where the teeth or angled projections within the holes can interact to cut any material in-between these angled projections.

Still referring to FIGS. 7-9, the cutting tip at the working end 16' of the device can have one of many different configurations. It should be appreciated that various embodiments of the inner cutting member 38' and the tubular outer cutting member 40' can be designed to create various embodiments of combination cutting tips, including symmetrical or asymmetrical designs. The inner cutting member 38' and the tubular outer cutting member 40' can both include one or more holes 36', 42' on the respective inner 38' and outer 40' tubes. For example, the inner cutting member 38' can include two or three holes 42' that surround the tube (FIG. 7A). The inner cutting member 38' can have one hole 42' on one side, for example, the top side, and one hole 42' on an opposite side, for ° example, the bottom side. The two or more holes 42' can be equally spaced apart around the inner tube 38'. Other embodiments have different spacing between the holes 42'.

Referring to FIG. 7A, the working end 16 can be configured such that there is always an opening into the working end 16. For example, where the inner tube 38' is rotated with respect to the outer tube 40' the exposure of hole 42' on the top side can be decreasing relative to hole 36' while the exposure of hole 42' on the bottom side can be increasing relative to the hole 36'. In an embodiment, the dual openings 42' on opposite sides of inner tube 38' can be advantageous because this configuration allows for a possible continuous vacuum to be applied through opening 36', as illustrated in FIG. 7A. As inner tube 38' rotates within outer tube 40', a first opening 42' will cut into tissue 112 and rotate out of view from the opening 36'. As the first opening 42' rotates out of view, the second opening 42' on the opposite side of inner tube 38' comes into view of opening 36' and provides aspiration through opening 36'. In an embodiment, the dual openings 42' are configured such that at least one of the dual openings 42' is exposed to opening 36' to provide aspiration through opening 36'. This configuration can provide for continuous aspiration through the opening 36'. A continuous vacuum through opening 36' allows the opening 36' to continuously grasp the tissue 112, 122 while cutting the tissue, thereby preventing the tissue 112, 122 from being projected into the retina or other area of the eye during tissue cutting. Prevention of tissue projection can be helpful in avoiding injury to sensitive tissue structures in the eye.

As illustrated, each of the holes 36', 42' on the respective inner 38' and outer 40' tubes includes one or more teeth, angled projections, or points. In some embodiments, the points are formed by two intersecting arcs forming part of the perimeter of the hole 36', 42'. The perimeter of the hole 36', 42' can be beveled, serrated, or otherwise sharpened to provide cutting edges. In some embodiments, at least a portion of the perimeter of the hole 36', 42' is curved or arcuate. In an embodiment, such angled projections can be advantageous in gripping or holding onto tissue 112, 122 during tissue cutting, thereby preventing injury or damage caused by tissue being projected into sensitive tissue structures during tissue cutting.

In FIG. 8, the inner tube 38' is shown. The hole 42' in the inner tube 38' can have a "snowman" configuration with three generally circular or elliptical cutouts. The distal most elliptical cutout can be smaller than the other two. The proximal most elliptical cutout can be the largest. Other configurations are also possible, for example, the hole 42' can comprise triangular cutouts, rectangular cutouts, diamond cutouts, or the like.

In FIG. 9, the outer tube 40' is shown. The hole 36' in the outer tube 40' can have a configuration with two generally circular or elliptical cutouts. The distal most elliptical cutout can be smaller than the proximal most elliptical cutout. Other configurations are also possible, for example, the hole 36' can comprise triangular cutouts, rectangular cutouts, diamond cutouts, or the like.

The edges of the holes 36', 42' of the outer tube 40' and the inner tube 38' can function as a pair of scissors or can produce a sawing effect to cut the tissue, independent of whether the cutting tubes move linearly or radially with respect to one another.

The configuration shown in FIGS. 7-9 could further include one or more aspiration holes 36A as illustrated and described with respect to FIGS. 3-6.

It should be appreciated that, in contrast to ultrasonic phacoemulsification devices, embodiments of the ocular lens cutting devices described herein can be constructed of low-cost materials such that the ocular lens cutting device can be disposed of after a single surgery, thus eliminating contamination and infection risks due to repetitive use of the device without proper sterilization. In addition, embodiments of the ocular lens cutting device can operate at low power, which reduces the risk of overheating or burning the cornea during surgery.

The embodiments herein illustrate ocular lens cutting devices and morcellation devices that can be portable, disposable, robust, low-power, cost effective, and can morcellate and/or remove tissue from a patient. Embodiments of the phacomorcellation devices described herein can advantageously be configured to prevent lens fragments from being projected toward a posterior portion of the eye, thereby preventing potential damage to the retina and other posterior eye structures. In an embodiment, this advantage is accomplished by capturing, and continuously drawing in and holding onto the lens fragment or other tissue while the cutting device morcellates and breaks up the substance into smaller pieces for removal through the inner lumen of the cutting device. Without the continuous drawing in and holding onto the lens fragment and other tissue, a cutting instrument may cut into the substance and remove a piece of the substance while the remaining portion of the substance is projected away from the cutting instrument and potentially towards the retina or other posterior eye structures. Accordingly, the embodiments disclosed herein can be advantageous in that the substance can be continuously held while cutting thereby preventing portions of the substance from being projected into the posterior portion of the eye.

Although this invention has been disclosed in the context of certain embodiments and examples, it will be understood by those skilled in the art that the invention extends beyond the disclosed embodiments to other alternative embodiments and/or uses of the invention and obvious modifications and equivalents thereof. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the invention should not be limited by the above description, but should be determined only by the claims.

What is claimed is:

1. An ocular cutting device comprising:
a housing having a motor positioned within the housing;
an aspiration line; and
a working end coupled to the aspiration line, the working end comprising:
   an outer sleeve member coupled in fixed relationship to the housing and having a proximal end and a distal end, the proximal end coupled to the housing, the distal end having first and second openings, the first opening having a first cutting edge; and
   an inner sleeve member having a proximal end and a distal end, the inner sleeve member positioned within the outer sleeve member, the motor operatively coupled to the proximal end to move the inner sleeve member relative to the outer sleeve member, the inner sleeve member having a third opening with a second cutting edge and a fourth opening in the distal end of the inner sleeve member, wherein the third opening is smaller than the first opening and the first opening and third opening are configured to interact to cut tissue between the first and second cutting edges; and
   wherein the second opening of the outer sleeve is configured to remain unobstructed by the movement of the inner sleeve such that a vacuum applied to the working end through the aspiration line allows the second opening to hold a tissue mass at a first location of the tissue mass while the tissue mass is cut and removed by the working end at a second location of the tissue mass spaced from the first location.

2. The device of claim 1, wherein the second opening is proximal to the first opening and where the inner sleeve member has an elongated opening corresponding to the second opening such that the second opening remains unobstructed by the movement of the inner sleeve.

3. The device of claim 1, wherein the aspiration line is coupled to the housing.

4. The device of claim 1, wherein a portion the aspiration line comprises a part of the housing.

5. The device of claim 1, wherein the first opening is located proximal to the second opening on the outer sleeve.

6. The device of claim 1, wherein the outer sleeve comprises a tubular, cylindrical member.

7. The device of claim 1, wherein the fourth opening includes a third cutting edge, the fourth opening configured to interact with the first opening to cut tissue between the first and third cutting edges.

8. The device of claim 7, wherein the fourth opening has a center axis perpendicular to the axis of the inner sleeve.

9. The device of claim 1, wherein the first opening comprises three generally circular or elliptical cutouts and the third opening comprises two generally circular or elliptical cutouts.

10. The device of claim 1, wherein the inner sleeve is configured for either linear or rotational movement with respect to the outer sleeve.

11. A method of using an ocular cutting device during surgery of the eye, the method comprising:
advancing a distal end of an ocular cutting device into a surgical site within the eye, the ocular cutting device having:
   an outer tubular cutting member having first and second openings at the distal end, the first opening having a first cutting edge;
   an inner cutting member having a third opening with a second cutting edge and a fourth opening in a distal end of the inner sleeve member, wherein the third opening is smaller than the first opening; and
   an aspiration line configured to apply a vacuum to the distal end of the ocular cutting device at the first and second openings;
applying a vacuum to the distal end of the ocular cutting device at the first and second openings;
grasping a lens of an eye with the suction from the vacuum at the first and/or second openings of the ocular cutting device;
drawing a first portion of the lens into the first opening in the outer tubular cutting member;
moving the inner cutting member with respect to the outer tubular cutting member and cutting off the first portion of the lens at the first opening to create a first lens fragment, while at the second opening, the lens remains grasped by the ocular cutting device; and
removing the first lens fragment from the surgical site through suction and through the fourth opening and the aspiration line.

12. The method of claim 11, wherein moving the inner cutting member with respect to the outer tubular cutting member comprises moving the inner cutting member in a linear manner or a rotational manner with respect to the outer tubular cutting member.

13. The method of claim 11, further comprising drawing a second portion of the lens into the first opening in the outer tubular cutting member; and
fragmenting the second portion of the lens by moving the inner cutting member with respect to the outer tubular cutting member and cutting off the second portion of the lens at the first opening to create a second lens fragment while at the second opening, the lens remains grasped by the ocular cutting device.

14. The method of claim 11, wherein the inner cutting member further comprises a tubular member such that removing the lens fragment from the surgical site through suction and through the outer tubular cutting member further comprises removing the lens fragment through the inner cutting member.

* * * * *